US012697310B2

(12) United States Patent
Lopachin et al.

(10) Patent No.: US 12,697,310 B2
(45) Date of Patent: *Aug. 4, 2026

(54) MULTIFUNCTIONAL CYTOPROTECTANT FOR TREATMENT OF PATHOGENIC PROCESSES MEDIATED BY OXIDATIVE STRESS AND TOXIC ELECTROPHILES

(71) Applicant: MONTEFIORE MEDICAL CENTER, Bronx, NY (US)

(72) Inventors: Richard M Lopachin, New Rochelle, NY (US); Terrence Gavin; Brian Geohagen, Bronx, NY (US)

(73) Assignee: MONTEFIORE MEDICAL CENTER, Bronx, NY (US)

( * ) Notice: Subject to any disclaimer, the term of this patent is extended or adjusted under 35 U.S.C. 154(b) by 492 days.

This patent is subject to a terminal disclaimer.

(21) Appl. No.: 17/816,980

(22) Filed: Aug. 2, 2022

(65) Prior Publication Data

US 2023/0133011 A1 May 4, 2023

Related U.S. Application Data

(63) Continuation of application No. 15/735,214, filed as application No. PCT/US2016/039487 on Jun. 27, 2016, now Pat. No. 11,413,255.

(60) Provisional application No. 62/185,801, filed on Jun. 29, 2015.

(51) Int. Cl.

| | |
|---|---|
| ***A61K 31/167*** | (2006.01) |
| ***A01N 1/126*** | (2025.01) |
| ***A61K 31/095*** | (2006.01) |
| ***A61K 31/12*** | (2006.01) |
| ***A61K 31/122*** | (2006.01) |
| ***A61K 31/191*** | (2006.01) |
| ***A61K 31/36*** | (2006.01) |
| ***A61K 31/381*** | (2006.01) |
| ***A61K 31/402*** | (2006.01) |
| ***A61K 31/495*** | (2006.01) |
| ***A61K 31/5375*** | (2006.01) |
| ***A61P 39/06*** | (2006.01) |
| ***C07C 49/78*** | (2006.01) |
| ***C07C 49/80*** | (2006.01) |
| ***C07C 49/807*** | (2006.01) |
| ***C07C 49/82*** | (2006.01) |
| ***C07C 49/825*** | (2006.01) |
| ***C07C 49/835*** | (2006.01) |
| ***C07C 49/84*** | (2006.01) |
| ***C07C 233/33*** | (2006.01) |
| ***C07C 323/22*** | (2006.01) |
| ***C07D 207/04*** | (2006.01) |
| ***C07D 207/325*** | (2006.01) |
| ***C07D 295/112*** | (2006.01) |
| ***C07D 333/22*** | (2006.01) |

(52) U.S. Cl.

CPC .............. *A61K 31/12* (2013.01); *A01N 1/126* (2025.01); *A61K 31/095* (2013.01); *A61K 31/167* (2013.01); *A61K 31/36* (2013.01); *A61K 31/381* (2013.01); *A61K 31/402* (2013.01); *A61K 31/495* (2013.01); *A61K 31/5375* (2013.01); *A61P 39/06* (2018.01); *C07C 49/80* (2013.01); *C07C 49/807* (2013.01); *C07C 49/825* (2013.01); *C07C 49/84* (2013.01); *C07C 233/33* (2013.01); *C07C 323/22* (2013.01); *C07D 207/04* (2013.01); *C07D 207/325* (2013.01); *C07D 295/112* (2013.01); *C07D 333/22* (2013.01)

(58) Field of Classification Search

CPC .. A61K 31/167; A61K 31/191; A61K 31/122; A61K 31/12; A61K 31/05; A61K 2300/00; A61K 31/095; A61K 31/36; A61K 31/495; C07C 49/825; C07C 49/82; C07C 49/835; C07C 49/78; C07C 233/33; C07C 323/22

See application file for complete search history.

(56) References Cited

U.S. PATENT DOCUMENTS

| | | | | |
|---|---|---|---|---|
| 5,877,210 | A | 3/1999 | Schieven | |
| 8,034,838 | B2 | 10/2011 | Thompson et al. | |
| 8,835,510 | B2 | 9/2014 | LoPachin et al. | |
| 10,104,882 | B2 * | 10/2018 | LoPachin ............... | A61K 31/05 |
| 11,413,255 | B2 * | 8/2022 | LoPachin ............ | A61K 31/495 |
| 2008/0139496 | A1 | 6/2008 | Prendergast | |
| 2008/0254130 | A1 | 10/2008 | Gupta | |
| 2013/0116337 | A1 | 5/2013 | LoPachin et al. | |
| 2013/0267474 | A1 | 10/2013 | Seeram et al. | |

(Continued)

FOREIGN PATENT DOCUMENTS

| | | | |
|---|---|---|---|
| WO | 0220500 | A2 | 3/2002 |
| WO | 2011156181 | A1 | 12/2011 |
| WO | 2014179187 | A1 | 11/2014 |

OTHER PUBLICATIONS

Ferreira, E. A., E. Gris, K. Felipe, J. Correia, E. Cargnin-Ferreira, D. Filho and R. Pedrosa, "Potent hepatoprotective effect in CCI4-induced hepatic injury in mice of phloroacetophenone from Myrcia multiflora", Libyan J Med (2010), 5: 4891. (Year: 2010).*

(Continued)

*Primary Examiner* — Kamal A Saeed
*Assistant Examiner* — Sagar Patel
(74) *Attorney, Agent, or Firm* — Asburst Perkins Coie US LLP

(57) ABSTRACT

Methods, filters and compositions are disclosed for treating toxicity due to oxidative stress and toxic electrophiles.

15 Claims, 12 Drawing Sheets

(56) References Cited

U.S. PATENT DOCUMENTS

2016/0074339 A1 3/2016 LoPachin et al.
2022/0016051 A1* 1/2022 Lopachin ............. A61K 31/282

OTHER PUBLICATIONS

LoPachin, R., T. Gavin, B. Geohagen, L. Zhang, D. Casper, R. Lekhraj and D. Barber, "β-Dicarbonyl enolates: a new class of neuroprotectants", J. Neurochem. (2011), 116, pp. 132-143. (Year: 2010).*
Allegretti, P., M. de las Mercedes Schiavoni, E. Castro and J. Furlong, "Tautomeric Equilibria Studies by Mass Spectrometry", World Journ. Chem. (2007), 2 (2), pp. 25-62. (Year: 2007).*
Bentes et al., Structure of dihydrochalcones and related derivatives and their scavenging and antioxidant activity against oxygen and nitrogen radical species. Molecules 16: 2011, 1749-1760.
Brenn et al., (2014) St. John's Wort reduces beta-amyloid accumulation in a double transgenic Alzheimer's disease mouse model-role of P-glycoprotein. Brain Pathol 24: 1824. Epub Jun. 28, 2013.
Chang et al., "Antiplatelet effect of phloroglucinol is related to inhibition of cyclooxygenase, reactive oxygen species, ERK/p38 signaling and thromboxane A2 production." Toxicol App Pharmacol 263: 2012, 287-295.
Chassany et al., "Acute exacerbation of pain in irritable bowel syndrome: efficacy of phloroglucinol/trimethyphloroglucinol—a randomized double-blind, placebo-controlled study." 2007, Aliment Pharmacol. 25: 1115-1123.
Chen et al., "Cytochrome P450 3A4-mediated bioactivation of raloxifene: Irreversible enzyme inhibition and thiol adduct formation." Chem Res Toxicol 15: 2002, 907-914.
Dinamarca et al., "Hyperforin prevents B-amyloid neurotoxicity and spatial memory impairments by disaggregation of Alzheimer's amyloid-b-deposits." 2006, Mole Physch. 11: 1032-1048.
Ferreira et al., "Potent hepatoprotective effect in CC14-induced hepatic injury in mice of phloroacetophenone from Myrcia multiflora." Libyan J Med 5: 4891-4896. 2010.
Galati et al., "Potential toxicity of flavonoids and other dietary phenolics: significance for the chemopreventive and anticancer properties." Free Rad. Biol. Med 37: 287-303. 2004.
Geohagen et al., "Enolate-Forming Phloretin Pharmacophores: Hepatoprotection in an Experimental Model of Drug-Induced Toxicity." J Pharmacol. Exp. Ther. 357, epub 2016.
Griffith et al., "Neurobiological effects of hyperforin and its potential in Alzheimer's disease therapy." Curr Ivfed Chem 17: 391-406. 2010.
Harsanyi et al., "2,6-Dihydroxy-4-Pyrrolidinyl-Acetophenone and Its Complex With Pyrrolidine." Heterocyc. Comm. 2002, 8(3), pp. 255-258.
Hatcher et al., "Curcumin: from ancient medicine to current clinical trials." Cell Mal. Life Sci. 65: 1631-1652. 2008.
Head, E., "Oxidative damage and cognitive dysfunction: antioxidant treatments to promote healthy brain aging." Neurochem. Res. 34: 670-678. 2009.
International Search Report and Written Opinion mailed Nov. 4, 2016 in International Patent Application No. PCT/US16/39487, 12 pages.
Iqbal et al., "Alzheimer's disease: a multifunctional disorder seeking multitherapies." Alzheimer & Dementia 6: 420-424. 2010.
Jaeschke et al., "Caveats of using acetaminophen hepatotoxicity models for natural product testing." Tax Letters 215: 40-41. 2012.
Kamat et al., "Antioxidants in central nervous system diseases: preclinical promise and translational challenges." J Alzheimers Dis. 15: 473-493. 2008.
Kim et al., "Effect of phloroglucinol on oxidative stress and inflammation." Food Chem Toxicol 48: 2925-2933. 2010.
Kim et al., "Phloroglucinol exerts protective effects against oxidative stress-induced cell damage in SH-SY5Y cells." J Pharmacol Sci 119: 186-192. 2012.
Kung et al. "Dihydroxylphenyl amides as inhibitors of the Hsp90 molecular chaperone." Bioorg. Med. Chem. Lett. 18 (2008) pp. 6273-6278.
Lambert et al., Possible controversy over dietary polyphenols: benefits vs risks. Chem Res Toxicol 20: 583-585. 2007.
Lopachin et al., "Application of the hard and soft acids and bases (HSAB) theory to toxicant-target interactions." Chem Res Toxicol 25: 239-251. 2012.
Lopachin et al., "B-Dicarbony 1 enolates: a new class of neuroprotectants." J Neurochem 116: 132-143. 2011.
Lopachin et al., "Molecular mechanisms of aldehyde toxicity: a chemical perspective." Chem. Res. Toxicol. 27, 1081-1091. 2014.
Mammino, L., "Investigation of the antioxidant properties of hyperjovinol A through its Cu(II) coordination ability." J A1olModel 19: 2127-2142. 2013.
Mathiesen et al., "Hydrogen bond formation as basis for radical scavenging activity: a structure-activity study of C-methylated dihydrochalcones from Myrica gale and structurally related acetophenones." Free Rad Biol Med 22: 307-311. 1997.
Piao et al., "Phloroglucinol inhibits ultraviolet B radiation-induced oxidative stress in the mouse skin." Int J Rad Biol. 2014.
Piyachaturawat et al., "Evaluation of the acute and subacute toxicity of a choleretic phloracetophenone in experimental animals." Toxic. Lett. 129, pp. 123-132, 2002.
Rezk et al., "The antioxidant activity of phloretin: the disclosure of a new antioxidant pharmacophore in flavonoids." Biochem Biophys Res Comm. 295: 9-13. 2002.
Ryu et al., "Phloroglucinol attenuates motor functional deficits in an animal model of Parkinson's disease by enhancing Nrf2 activity." PLoS One 8: e71178. 2013.
Sappington et al., "The ethyl pyruvate analogues, diethy oxaloproprionate, 2-acetamidoacrylate, and methyl-2-acetamidoacrylate, exhibit anti-inflammatory properties in vivo and/or in vitro." BiochemPharmacol 70, 1579-1592. 2005.
Schaefer et al., "Polyphenolic apple juice extracts and their major constituents reduce oxidative damage in human colon cell lines." Mol. Nutr. Food Res. 2006, 50, pp. 24-33.
Singh et al., "Challenges for research on polyphenols from foods in Alzheimer's disease: bioavailability, metabolism and cellular and molecular mechanisms." J Agric Food Chem 56: 4855-4873. 2008.
Singh et al., "Phloroglucinol compounds of therapeutic interest: global patent and technology status." Exp Opin. Ther Patents 19: 847-866.2009.
Singh et al., "Phlororglucinol compounds of natural origin." Nat. Prod. Rep. 23: 558-591. 2006.
So et al., "Phloroglucinol attenuates free radical-induced oxidative stress." Prev Nutr Food Sci 19: 129-135. 2014.
STN Registry database entry: CAS RN 100942-39-0 (Entered STN: Mar. 22, 1986).
STN Registry database entry: CAS RN 1610500-76-9 (Entered STN: Jun. 11, 2014).
STN Registry database entry: CAS RN 206194-38-9 (Entered STN: Jun. 2, 1998).
STN Registry database entry: CAS RN 266338-15-2 (Entered STN: May 24, 2000).
STN Registry database entry: CAS RN 404011-08-1 (Entered STN: Apr. 4, 2002).
Tyrell et al., "The synthesis and anticancer effects of a range of natural and unnatural hop B-acids on breast cancer cells." Phytochemistry Letters 5 (2012), pp. 144-149.
Wurglics et al., "Hepericum perforatum: a modem herbal antidepressant: pharmacokinetics of active ingredients." Clin Pharmacokinet 45: 449-468. 2006.
Youdim et al., "A possible emergmg role of phytochemicals in improving age-related neurological dysfunctions: a multiplicity of effects." Free Rad Biol. Med. 30: 583-594. 2001.
Zanoli, P., "Role of hyperforin in the pharmacological activities of St. John's Wort." CNS Drug Rev. 10: 203-218. 2004.
Zhu et al., "In vitro attenuation of acrolein-induced toxicity by phloretin, a phenolic compound from apple." Food Chem. 135: 1762-1768. 2012.

* cited by examiner

Phloretin 1,3,5- Trihydroxybenzene
(Phloroglucinol)

2',4',6'-Trihydroxyacetophenone 4-acetyl-2,6-dihydroxy acetophenone (4-NAHA)

MULTIFUNCTIONAL CYTOPROTECTANT FOR TREATMENT OF PATHOGENIC PROCESSES MEDIATED BY OXIDATIVE STRESS AND TOXIC ELECTROPHILES

CROSS-REFERENCE TO RELATED APPLICATIONS

This application is a continuation of U.S. patent application Ser. No. 15/735,214, filed Dec. 11, 2017 which is a 371 of PCT/US2016/39487, filed Jun. 27, 2016 which claims the benefit of U.S. Provisional Patent Application No. 62/185,801, filed on Jun. 29, 2015, the contents of which are herein incorporated by reference.

STATEMENT OF GOVERNMENT SUPPORT

This invention was made with government support under grant number ES003830 awarded by the National Institutes of Health. The government has certain rights in the invention.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

Oxidative stress injury and electrophile toxicities are significant pathogenic factors that impact the quality of human health. Numerous pathogenic conditions have oxidative stress as a common molecular etiology, such as, e.g., atherosclerosis, ischemia/reperfusion (FR) injury, diabetes, spinal cord injury and Alzheimer disease. In addition, drug toxicity can occur due to administration of drugs that are electrophilic (e.g., cisplatin) or those that are transformed to a reactive electrophilic metabolite (e.g., acetaminophen). Furthermore, certain diseases (e.g., atherosclerosis, diabetes) can be accelerated by exposure to electrophilic environmental pollutants.

Cellular oxidative stress plays a preeminent role in many pathophysiological processes and therefore development of an effective therapeutic approach would have broad impact on human health and disease prevention. Oxidative stress is characterized by the generation of reactive oxygen (ROS) and nitrogen (RNS) species (e.g., peroxynitrite, superoxide and hydroxyl radicals) that can damage macromolecules and cellular organelles. The reaction of these free radicals with lipid-rich membranes can also produce highly toxic unsaturated aldehyde electrophiles (e.g., acrolein, 4-hydroxy-2-nonenal) that cause cell injury by depleting glutathione (GSH) and by forming adducts with specific cysteine residues that regulate protein function. Evidence now indicates that the toxic consequences of oxidative stress are, in fact, mediated by unsaturated aldehydes. Given the complexity of this toxic cascade, there is almost uniform agreement among investigators that effective pharmacotherapeutic management of oxidative stress-related diseases will require either a "cocktail" of several drugs or a multifunctional compound that can block the pathophysiological cascade at several rate-limiting steps. Although results from initial experimental studies were supportive, many of the potential pharmacotherapeutic approaches (e.g., α-tocopherol, resveratrol, N-acetyl cysteine) were either palliative or had disappointing clinical effectiveness.

With respect to acquired toxicities due to administration of electrophilic drugs or environmental toxicant exposure, effective pharmacotherapeutic approaches are limited and, since acceleration of endogenous disease processes by exposure to environmental toxicants has been only recently recognized, no corresponding therapies exist.

The present invention addresses the need for methods and compositions for treating pathogenic processes mediated by oxidative stress and toxic electrophiles.

SUMMARY OF THE INVENTION

Compositions, filters and methods are disclosed for treating toxicity due to oxidative stress and toxic electrophiles, where the compositions comprise a compound of formula (I) as described herein and the methods comprise the use of a compound of formula (I) as described herein.

DETAILED DESCRIPTION OF THE INVENTION

Figure 1:
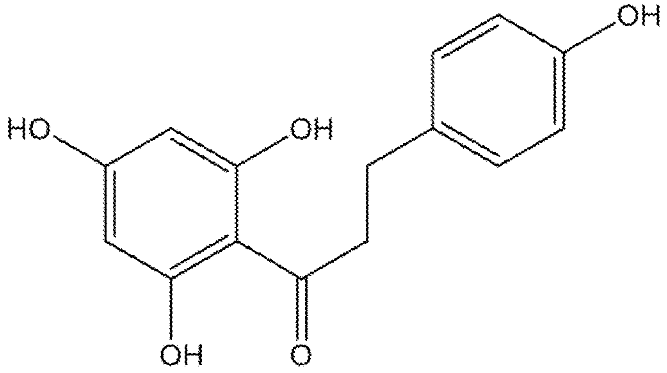
FIG. 1. Structures of phloretin and pharmacophores 1,3,5-trihydroxybenzene (Phloroglucinol, PG), 2',4',6'-trihydroxyacetophenone (THA) and 4-acetyl-2,6-dihydroxy acetophenone (4-NAHA).
Figure 1:
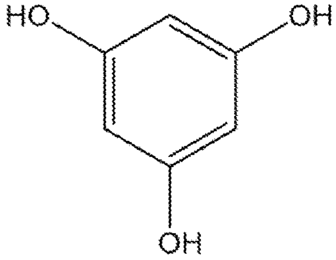
Figure 1:
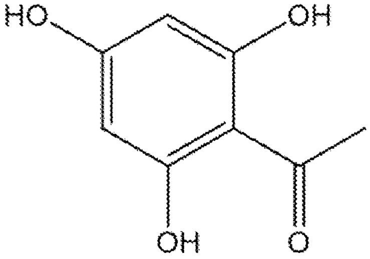
Figure 1:
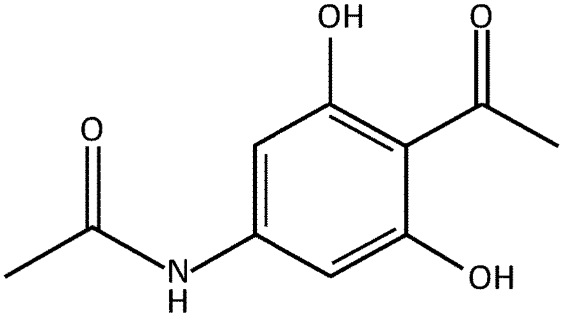

The present invention provides a method of preventing or treating toxicity due to a therapeutic agent or an agent that causes oxidative cellular damage in a subject receiving the agent comprising administering to the subject a compound of formula (I) in an amount effective to prevent or reduce toxicity due to the agent, wherein the compound has the structure:

(I)

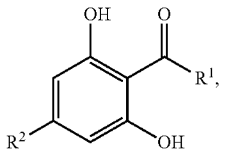

wherein $R^1$ and $R^3$ are independently alkyl, alkenyl, aryl, aralkyl, cyclic, heteroaryl, heteroaralkyl or heterocyclic;

$R^2$ is OH, $NH_2$, $NHCOR^3$, N-alkyl, N,N-dialkyl, cyclic N,N-dialkyl, SH, S-alkyl, S-aryl, aryl, heteroaryl, or $NR^4R^5$; and $R^4$ and $R^5$ are independently alkyl or N-alkyl, and $R^4$ and $R^5$ can form a ring with each other, and any ring so formed may be aromatic or heteroaromatic, and any ring so formed may contain one or more N, O and/or S atoms;

wherein any aryl, aralkyl, cyclic, heteroaryl, heteroaralkyl, heterocyclic or ring can be independently substituted with =O, OH, halogen, $CH_3$ or $NH_2$;

wherein any alkyl can independently be branched or unbranched;

or a tautomer thereof; or a geometric or optical isomer thereof; or racemate thereof; or a pharmaceutically acceptable salt thereof.

Examples of such therapeutic agents include, but are not limited to, acetaminophen, diclofenac, cyclophosphamide, valproic acid, clopidogrel, esomeprazole, atorvastatin, duloxetine, raloxifene, platinum containing antineoplatstic agents such as cisplatin, and radiation used in radiation therapy. Examples of agents that can cause oxidative cellular damage include, but are not limited to, tobacco smoke, acrolein, alcohol such as ethanol, and radiocontrast agents.

Preferably, the agent is a polarizable electrophile.

The toxicity caused by the agent can be hepatotoxicity, such as acetaminophen-induced hepatotoxicity, neurotoxicity, such as cisplatin-induced neurotoxicity, or any toxicity due to oxidative cellular stress.

The compound can be administered to the subject at the same time that the agent is administered to the subject. The compound and the agent can be administered in the same formulation. The compound can be administered to the subject before the agent is administered to the subject or after the agent is administered to the subject.

The invention also provides a method of treating a disease or disorder that is improved through administration of N-acetylcysteine to a subject, the method comprising administering to the subject a compound of formula (I) in an amount effective to improve a sign or symptom of the disease or disorder, wherein the compound has the structure:

(I)

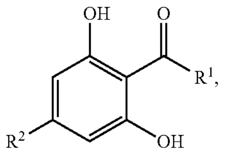

wherein $R^1$ and $R^3$ are independently alkyl, alkenyl, aryl, aralkyl, cyclic, heteroaryl, heteroaralkyl or heterocyclic;

$R^2$ is OH, $NH_2$, $NHCOR^3$, N-alkyl, N,N-dialkyl, cyclic N,N-dialkyl, SH, S-alkyl, S-aryl, aryl, heteroaryl, or $NR^4R^5$; and $R^4$ and $R^5$ are independently alkyl or N-alkyl, and $R^4$ and $R^5$ can form a ring with each other, and any ring so formed may be aromatic or heteroaromatic, and any ring so formed may contain one or more N, O and/or S atoms;

wherein any aryl, aralkyl, cyclic, heteroaryl, heteroaralkyl, heterocyclic or ring can be independently substituted with =O, OH, halogen, $CH_3$ or $NH_2$;

wherein any alkyl can independently be branched or unbranched;

or a tautomer thereof; or a geometric or optical isomer thereof; or racemate thereof; or a pharmaceutically acceptable salt thereof.

Examples of such diseases or disorders include, but are not limited to, viral infections, such as human immunodeficiency virus infection/acquired immunodeficiency syndrome (HIV/AIDS) and influenza, pulmonary diseases, such as cystic fibrosis and chronic obstructive pulmonary disease (COPD), and emotional disorders, such as obsessive-compulsive syndrome and trichotillomania.

Signs and symptoms of various diseases and disorders are well known to those skilled in the art. Signs and symptoms of HIV/AIDS include, but are not limited to, fever, large tender lymph nodes, throat inflammation, rash, headache, sores of the mouth and genitals, neurological symptoms of peripheral neuropathy, pneumocystis pneumonia, HIV wasting syndrome, esophageal candidiasis, and recurring respiratory tract infections. Signs and symptoms of influenza include, but are not limited to, chills, fever, runny nose, sore throat, muscle pains, headache, coughing, and weakness and fatigue. Signs and symptoms of cystic fibrosis include, but are not limited to, difficulty breathing. Signs and symptoms of chronic obstructive pulmonary disease include, but are not limited to, shortness of breath. Signs and symptoms of obsessive-compulsive syndrome include, but are not limited to, uneasiness, apprehension, fear or worry, repetitive behaviors, excessive washing or cleaning, and nervous rituals. Signs and symptoms of trichotillomania include, but are not limited to, pulling out and eating one's own hair.

The invention also provides a method of preventing or treating liver ischemia-reperfusion injury in a subject comprising administering to the subject a compound of formula (I) in an amount effective to prevent or reduce liver ischemia-reperfusion injury, wherein the compound has the structure:

(I)

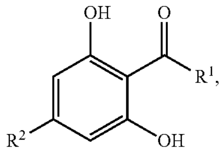

wherein $R^1$ and $R^3$ are independently alkyl, alkenyl, aryl, aralkyl, cyclic, heteroaryl, heteroaralkyl or heterocyclic;

$R^2$ is OH, $NH_2$, $NHCOR^3$, N-alkyl, N,N-dialkyl, cyclic N,N-dialkyl, SH, S-alkyl, S-aryl, aryl, heteroaryl, or $NR^4R^5$; and $R^4$ and $R^5$ are independently alkyl or N-alkyl, and $R^4$ and $R^5$ can form a ring with each other, and any ring so formed may be aromatic or heteroaromatic, and any ring so formed may contain one or more N, O and/or S atoms;

wherein any aryl, aralkyl, cyclic, heteroaryl, heteroaralkyl, heterocyclic or ring can be independently substituted with =O, OH, halogen, $CH_3$ or $NH_2$;

wherein any alkyl can independently be branched or unbranched;

or a tautomer thereof; or a geometric or optical isomer thereof; or racemate thereof; or a pharmaceutically acceptable salt thereof.

The subject can be at risk for liver ischemia-reperfusion injury, for example, because the subject is undergoing removal of at least part of the liver or because the subject is undergoing liver transplantation. Alternatively, the subject can have, for example, a disease that reduces blood flow to the liver, such as, e.g., stroke or coronary artery occlusion. Preferably, administration of the compound of formula (I) to the subject is effective to reduce elevated serum levels of one or more of alanine aminotransferase (ALT), aspartate aminotransferase (AST) and lactate dehydrogenase (LDH).

Also provided is a method of treating a subject with a disease or tissue injury mediated by cellular oxidative stress, wherein the disease or tissue injury is atherosclerosis, diabetes, Alzheimer's disease, stroke, lung damage associated with smoking (e.g., smoking a cigarette, cigar or pipe), or traumatic spinal cord injury, the method comprising administering to the subject a therapeutically effective amount of a compound of formula (I)

(I)

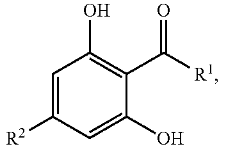

wherein $R^1$ and $R^3$ are independently alkyl, alkenyl, aryl, aralkyl, cyclic, heteroaryl, heteroaralkyl or heterocyclic;

$R^2$ is OH, $NH_2$, $NHCOR^3$, N-alkyl, N,N-dialkyl, cyclic N,N-dialkyl, SH, S-alkyl, S-aryl, aryl, heteroaryl, or $NR^4R^5$; and $R^4$ and $R^5$ are independently alkyl or N-alkyl, and $R^4$ and $R^5$ can form a ring with each other, and any ring so formed may be aromatic or heteroaromatic, and any ring so formed may contain one or more N, O and/or S atoms;

wherein any aryl, aralkyl, cyclic, heteroaryl, heteroaralkyl, heterocyclic or ring can be independently substituted with =O, OH, halogen, $CH_3$ or $NH_2$;

wherein any alkyl can independently be branched or unbranched;

or a tautomer thereof; or a geometric or optical isomer thereof; or racemate thereof; or a pharmaceutically acceptable salt thereof.

As used herein, to treat a subject with a disease or tissue injury mediated by cellular oxidative stress or a subject with an environmental toxicity due to an electrophilic toxicant or pollutant means to alleviate a sign or symptom associated with the disease, injury or environmental toxicity.

Still further provided is a method of providing a nutritional supplement to a subject comprising administering to the subject a compound of formula (I)

(I)

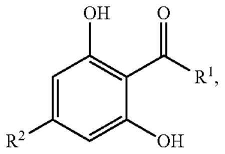

wherein $R^1$ and $R^3$ are independently alkyl, alkenyl, aryl, aralkyl, cyclic, heteroaryl, heteroaralkyl or heterocyclic;

$R^2$ is OH, $NH_2$, $NHCOR^3$, N-alkyl, N,N-dialkyl, cyclic N,N-dialkyl, SH, S-alkyl, S-aryl, aryl, heteroaryl, or $NR^4R^5$; and $R^4$ and $R^5$ are independently alkyl or N-alkyl, and $R^4$ and $R^5$ can form a ring with each other, and any ring so formed may be aromatic or heteroaromatic, and any ring so formed may contain one or more N, O and/or S atoms;

wherein any aryl, aralkyl, cyclic, heteroaryl, heteroaralkyl, heterocyclic or ring can be independently substituted with =O, OH, halogen, $CH_3$ or $NH_2$;

wherein any alkyl can independently be branched or unbranched;

or a tautomer thereof; or a geometric or optical isomer thereof; or racemate thereof; or a pharmaceutically acceptable salt thereof.

Also provided is a method of treating a subject with an environmental toxicity due to an electrophilic toxicant or pollutant, wherein the toxicant or pollutant is acrolein, acrylamide, methyl vinyl ketone, chlorpyrifos methyl-mercury, an $\alpha,\beta$-unsaturated aldehyde derivative, an $\alpha,\beta$-unsaturated carbonyl derivative, a heavy metal, an organophosphate insecticide, acrylamide contaminated well-water or an industrial acrylonitrile, the method comprising administering to the subject a therapeutically effective amount of a compound of formula (I)

(I)

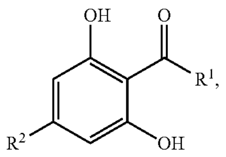

wherein $R^1$ and $R^3$ are independently alkyl, alkenyl, aryl, aralkyl, cyclic, heteroaryl, heteroaralkyl or heterocyclic;

$R^2$ is OH, $NH_2$, $NHCOR^3$, N-alkyl, N,N-dialkyl, cyclic N,N-dialkyl, SH, S-alkyl, S-aryl, aryl, heteroaryl, or $NR^4R^5$; and $R^4$ and $R^5$ are independently alkyl or N-alkyl, and $R^4$ and $R^5$ can form a ring with each other, and any ring so formed may be aromatic or heteroaromatic, and any ring so formed may contain one or more N, O and/or S atoms;

wherein any aryl, aralkyl, cyclic, heteroaryl, heteroaralkyl, heterocyclic or ring can be independently substituted with =O, OH, halogen, $CH_3$ or $NH_2$;

wherein any alkyl can independently be branched or unbranched;

or a tautomer thereof; or a geometric or optical isomer thereof; or racemate thereof; or a pharmaceutically acceptable salt thereof.

For example, the subject can have mercury (Hg), lead (Pb) or arsenic (As) poisoning.

An electrophile is attracted to electrons and participates in a chemical reaction by accepting an electron pair in order to bond to a nucleophile. A nucleophile forms a chemical bond to its reaction partner (the electrophile) by donating both bonding electrons.

The compound can be administered to a subject, for example, by parenteral administration or by oral administration.

Preferably, the compound prevents or reduces hepatotoxicity.

Still further provided is a method of treating the skin of a subject comprising administering to the skin of the subject a compound of formula (I)

(I)

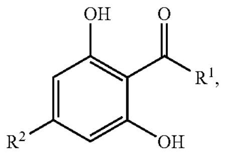

wherein $R^1$ and $R^3$ are independently alkyl, alkenyl, aryl, aralkyl, cyclic, heteroaryl, heteroaralkyl or heterocyclic;

$R^2$ is OH, $NH_2$, $NHCOR^3$, N-alkyl, N,N-dialkyl, cyclic N,N-dialkyl, SH, S-alkyl, S-aryl, aryl, heteroaryl, or $NR^4R^5$; and $R^4$ and $R^5$ are independently alkyl or N-alkyl, and $R^4$ and $R^5$ can form a ring with each other, and any ring so formed may be aromatic or heteroaromatic, and any ring so formed may contain one or more N, O and/or S atoms;

wherein any aryl, aralkyl, cyclic, heteroaryl, heteroaralkyl, heterocyclic or ring can be independently substituted with =O, OH, halogen, $CH_3$ or $NH_2$;

wherein any alkyl can independently be branched or unbranched;

or a tautomer thereof; or a geometric or optical isomer thereof; or racemate thereof; or a pharmaceutically acceptable salt thereof.

The compound can be used, for example, to prevent or treat an aging effect on the skin or to prevent or treat sun damage to the skin. For example, the compound can be used to treat or prevent wrinkles.

The invention further provides a method of increasing the viability of an organ for organ transplantation comprising adding to an organ preservation solution a compound of formula (I) in an amount effective to increase the viability of an organ for transplantation, wherein the compound has the structure:

(I)

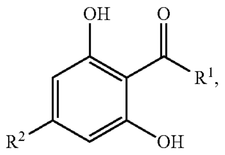

wherein $R^1$ and $R^3$ are independently alkyl, alkenyl, aryl, aralkyl, cyclic, heteroaryl, heteroaralkyl or heterocyclic;

$R^2$ is OH, $NH_2$, $NHCOR^3$, N-alkyl, N,N-dialkyl, cyclic N,N-dialkyl, SH, S-alkyl, S-aryl, aryl, heteroaryl, or $NR^4R^5$; and $R^4$ and $R^5$ are independently alkyl or N-alkyl, and $R^4$ and $R^5$ can form a ring with each other, and any ring so formed may be aromatic or heteroaromatic, and any ring so formed may contain one or more N, O and/or S atoms;

wherein any aryl, aralkyl, cyclic, heteroaryl, heteroaralkyl, heterocyclic or ring can be independently substituted with =O, OH, halogen, $CH_3$ or $NH_2$;

wherein any alkyl can independently be branched or unbranched;

or a tautomer thereof; or a geometric or optical isomer thereof; or racemate thereof; or a pharmaceutically acceptable salt thereof.

Examples of organ preservation solutions include, but are not limited to, the University of Wisconsin (UW) solution and Leeds and histidine-tryptophan-ketoglutarate (HTK) solution.

The invention also provides an organ preservation solution comprising a compound of formula (I) in an amount effective to increase the viability of an organ for transplantation, wherein the compound has the structure:

(I)

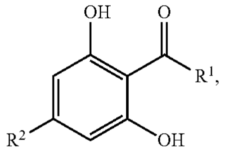

wherein $R^1$ and $R^3$ are independently alkyl, alkenyl, aryl, aralkyl, cyclic, heteroaryl, heteroaralkyl or heterocyclic;

$R^2$ is OH, $NH_2$, $NHCOR^3$, N-alkyl, N,N-dialkyl, cyclic N,N-dialkyl, SH, S-alkyl, S-aryl, aryl, heteroaryl, or $NR^4R^5$; and $R^4$ and $R^5$ are independently alkyl or N-alkyl, and $R^4$ and $R^5$ can form a ring with each other, and any ring so formed may be aromatic or heteroaromatic, and any ring so formed may contain one or more N, O and/or S atoms;

wherein any aryl, aralkyl, cyclic, heteroaryl, heteroaralkyl, heterocyclic or ring can be independently substituted with =O, OH, halogen, $CH_3$ or $NH_2$;

wherein any alkyl can independently be branched or unbranched;

or a tautomer thereof; or a geometric or optical isomer thereof; or racemate thereof; or a pharmaceutically acceptable salt thereof.

The invention further provides a composition for preventing and treating toxicity due to a therapeutic agent, the composition comprising the therapeutic agent and a compound of formula (I) in an amount effective to prevent or reduce toxicity due to the agent, wherein the compound has the structure:

(I)

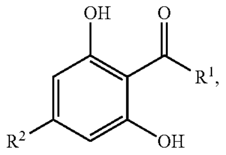

wherein $R^1$ and $R^3$ are independently alkyl, alkenyl, aryl, aralkyl, cyclic, heteroaryl, heteroaralkyl or heterocyclic;

$R^2$ is OH, $NH_2$, $NHCOR^3$, N-alkyl, N,N-dialkyl, cyclic N,N-dialkyl, SH, S-alkyl, S-aryl, aryl, heteroaryl, or $NR^4R^5$; and $R^4$ and $R^5$ are independently alkyl or N-alkyl, and $R^4$ and $R^5$ can form a ring with each other, and any ring so formed may be aromatic or heteroaromatic, and any ring so formed may contain one or more N, O and/or S atoms;

wherein any aryl, aralkyl, cyclic, heteroaryl, heteroaralkyl, heterocyclic or ring can be independently substituted with =O, OH, halogen, $CH_3$ or $NH_2$;

wherein any alkyl can independently be branched or unbranched;

or a tautomer thereof; or a geometric or optical isomer thereof; or racemate thereof; or a pharmaceutically acceptable salt thereof.

Examples of therapeutic agents include, but are not limited to, acetaminophen, diclofenac, cyclophosphamide, valproic acid, clopidogrel, atorvastatin, duloxetine, raloxifene and esomeprazole. Preferably, the therapeutic agent is a polarizable electrophile. Preferably, for oral administration, the composition is formulated with an enteric coating.

The toxicity can be, for example, hepatotoxicity, neurotoxicity, or toxicity due to oxidative cellular stress.

Also provided is a filter comprising a compound of formula (I) in an amount effective to prevent or reduce toxicity due to an environmental agent or toxin, wherein the compound has the structure:

(I)

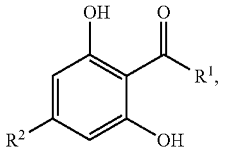

wherein $R^1$ and $R^3$ are independently alkyl, alkenyl, aryl, aralkyl, cyclic, heteroaryl, heteroaralkyl or heterocyclic;

$R^2$ is OH, $NH_2$, $NHCOR^3$, N-alkyl, N,N-dialkyl, cyclic N,N-dialkyl, SH, S-alkyl, S-aryl, aryl, heteroaryl, or $NR^4R^5$; and $R^4$ and $R^5$ are independently alkyl or N-alkyl, and $R^4$ and $R^5$ can form a ring with each other, and any ring so formed may be aromatic or heteroaromatic, and any ring so formed may contain one or more N, O and/or S atoms;

wherein any aryl, aralkyl, cyclic, heteroaryl, heteroaralkyl, heterocyclic or ring can be independently substituted with =O, OH, halogen, $CH_3$ or $NH_2$;

wherein any alkyl can independently be branched or unbranched;

or a tautomer thereof; or a geometric or optical isomer thereof; or racemate thereof;

or a pharmaceutically acceptable salt thereof.

The filter can be, for example, an air, water or breathing filter, such as used, for example, by fire fighters. The filter can be, for example, a filter for a cigarette, cigar or smoking pipe, wherein the compound of formula (I) is present in an amount effective to prevent or reduce toxicity due to smoke from a cigarette, cigar or smoking pipe. The filter can be configured, for example, for an end of a cigarette or cigar that is placed in a subject's mouth, or the filter can be configured to fit in a stem of a pipe or holder for a cigarette or cigar.

In any of the methods, the organ preservation solutions or compositions or filters disclosed herein, the compound can have the structure:

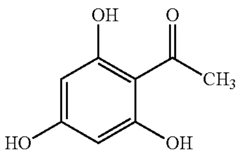

or

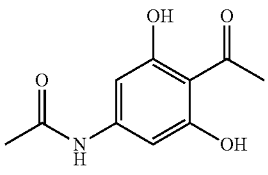

, or a pharmaceutically acceptable salt thereof.

The invention also provides a compound having the structure:

(I)

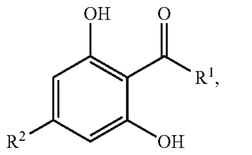

wherein

- $R^1$ and $R^3$ are independently alkyl, alkenyl, aryl, aralkyl, cyclic, heteroaryl, heteroaralkyl or heterocyclic;
- $R^2$ is $NH_2$, $NHCOR^3$, N-alkyl, N,N-dialkyl, cyclic N,N-dialkyl, SH, S-alkyl, S-aryl, aryl, heteroaryl, or $NR^4R^5$; and
- $R^4$ and $R^5$ are independently alkyl or N-alkyl, and $R^4$ and $R^5$ can form a ring with each other, and any ring so formed may be aromatic or heteroaromatic, and any ring so formed may contain one or more N, O and/or S atoms;
- wherein any aryl, aralkyl, cyclic, heteroaryl, heteroaralkyl, heterocyclic or ring can be independently substituted with =O, OH, halogen, $CH_3$ or $NH_2$;
- wherein any alkyl can independently be branched or unbranched;
- or a tautomer thereof; or a geometric or optical isomer thereof; or racemate thereof; or a pharmaceutically acceptable salt thereof.

In any of the methods, the organ preservation solutions, compositions, filters or compounds disclosed herein, any alkyl can be independently C1-C6 alkyl, for example C1-C3 alkyl or $CH_3$. Similarly, any aralkyl or heteroaralkyl can independently include for example C1-C6 alkyl, for example C1-C3 alkyl or C1 alkyl.

In any of the methods, the organ preservation solutions, compositions, filters or compounds disclosed herein, a ring formed between $R^4$ and $R^5$ can be a 4-12 member ring, for example a 4-7 member ring or a 5-6 member ring.

In any of the methods, the organ preservation solutions, compositions, filters or compounds disclosed herein, the compound can have the structure:

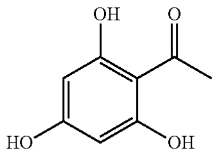
,
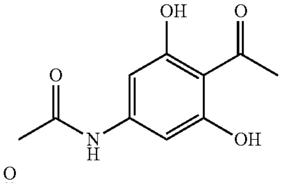
,
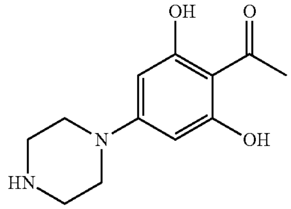
,
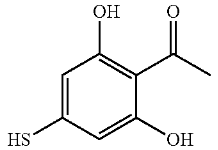
,
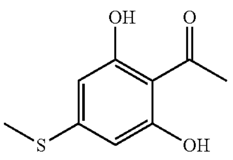
,
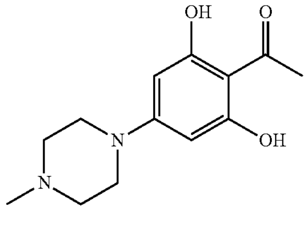
,

-continued

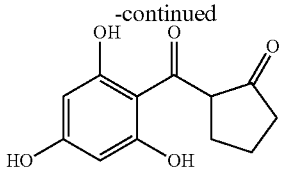
or
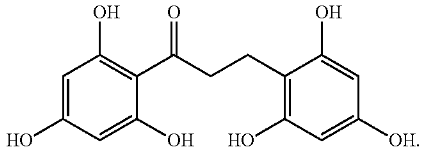

or a tautomer thereof; or a geometric or optical isomer thereof; or racemate thereof; or a pharmaceutically acceptable salt thereof.

Pharmaceutically acceptable salts that can be used include non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

Also provided is a pharmacological composition comprising any of the compounds disclosed herein and a pharmaceutically acceptable carrier.

The compounds can be administered to the subject in a pharmaceutical composition comprising a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. The pharmaceutically acceptable carrier used can depend on the route of administration. The pharmaceutical composition can be formulated for administration by any method known in the art, including but not limited to, oral administration, parenteral administration, intraperitoneal administration, intravenous administration, intramuscular administration, transdermal administration, intranasal administration, and administration through an osmotic mini-pump.

When the compound or composition is administered by oral administration, the compound or composition is preferably formulated with an enteric coating. Enteric coatings are well known in the art. The enteric coating can be stable at the acidic pH found in the stomach, but can break down in the alkaline environment of the small intestine. Materials used for enteric coatings include fatty acids, waxes and plant fibers.

The compounds can be applied to the skin, for example, in compositions formulated as skin creams, or as sustained release formulations or patches.

The compound can be administered to the subject at the same time that the agent is administered to the subject. In a preferred embodiment, the compound and the therapeutic agent are administered in the same formulation. In other embodiments, the compound is administered to the subject before and/or after the agent is administered to the subject.

The compound can be administered to a subject known to be at risk for liver ischemia-reperfusion injury before the onset of the ischemia, for example, before or at the start of a surgical procedure. The compound can also be administered to a subject during liver ischemia-reperfusion or as soon as possible after liver ischemia-reperfusion.

2',4',6'-trihydroxyacetophenone (THA) can be purchase commercially (e.g., Sigma-Aldrich).

All combinations of the various elements described herein, including all subsets, are within the scope of the invention unless otherwise indicated herein or otherwise clearly contradicted by context. Where a numerical range is provided herein for any parameter, it is understood that all numerical subsets of that numerical range, and all the individual integer values contained therein, are provided as part of the invention. Thus, C1-C6 alkyl includes, for example, the subset of alkyls which are 1-3 carbon atoms, the subset of alkyls which are 2-5 carbon atoms etc. as well as an alkyl which has 1 carbon atom, an alkyl which has 3 carbon atoms, an alkyl which has 6 carbon atom, etc.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example A—Biological Studies

Executive Summary

The invention involves the identification of 2',4',6'-trihydroxyacetophenone (THA; FIG. 1) as a highly efficacious cytoprotectant in animal models of oxidative stress. This is a completely unprecedented finding that became evident during studies of phytopolyphenol cytoprotection. The invention is expected to have a significant impact on the clinical management of many diseases and tissue injury conditions since oxidative stress is a ubiquitous pathophysiological process. A recently issued US patent (U.S. Pat. No. 8,835,510 B2) covers 1,3-dicarbonyl derivatives of the phytopolyphenol curcumin. THA is a derivative of the phytopolyphehol phloretin and possess a superior capacity to prevent oxidative stress. This potency is related to the ability of THA to attack the oxidative stress process at several steps, thereby directly and effectively alleviating cell injury.

Introduction

Oxidative stress-induced cell damage is a primary pathophysiological process underlying many diseases (e.g., atherosclerosis, stroke) and traumatic injuries (e.g., spinal cord injury). Because of corresponding molecular complexity, it has been difficult to identify specific components of the oxidative stress cascade that might be relevant therapeutic targets. Given the apparent primary role of reactive oxygen (ROS) and nitrogen (RNS) species in this process, antioxidants that trap free radicals, such as α-tocopherol and ascorbic acid, were initially considered as a possible pharmacological defense. Although animal studies were encouraging, corresponding clinical trials were mostly disappointing (Head, 2009; Kamat et al., 2008).

As an alternative pharmacotherapeutic strategy, many investigators considered a multifunctional approach to blockade of the oxidative stress cascade (Iqbal and Grundke-Iqbal, 2010; LoPachin et al., 2011; Youdim and Joseph, 2001). Plant-derived polyphenols such as curcumin, phloretin and resveratrol were considered based on their ability to impact oxidative stress at multiple levels. Indeed, these phytopolyphenols can trap reactive oxygen and nitrogen species, chelate metal ions ($Cu^{2+}$, $Fe^{2+}$) involved in the free radical-generating Fenton reaction and scavenge toxic unsaturated aldehydes (e.g., acrolein, 4-hydroxy-2-nonenal; Hatcher et al., 2008; Singh et al., 2008; Zhu et al., 2012). However, the therapeutic utility of the polyphenols is limited by toxicity, low bioavailability and chemical instability (Galati and O'Brien, 2004; Hatcher et al., 2008; Lambert et al., 2007). Thus, early research indicated that phloretin, a flavonoid found in apple skins, provided significant cytoprotection at low concentrations (100-250 μM) in several cell culture models of oxidative stress and electrophile (acrolein) toxicity (LoPachin et al., 2011). However, the concentration range for protection was very narrow, since higher phloretin concentrations were cytotoxic (LoPachin et al., 2011). More recently, a similar concentration-dependent cycle of phloretin protection/toxicity was demonstrated in acetaminophen (APAP)-exposed isolated hepatocytes (Geohagen et al., 2016). In a mouse model of APAP poisoning (500 mg/kg; p.o.) it was shown that a low intraperitoneal (i.p.) dose of phloretin (0.200 mmol/kg) provided marginal hepatoprotection. However, higher phloretin doses (0.40-2.40 mmol/kg) were associated with lethality when administered alone (data not illustrated), which precluded consideration as a hepatoprotectant.

Characterization of Phloretin Pharmacophores

Figures 2A, 2B:
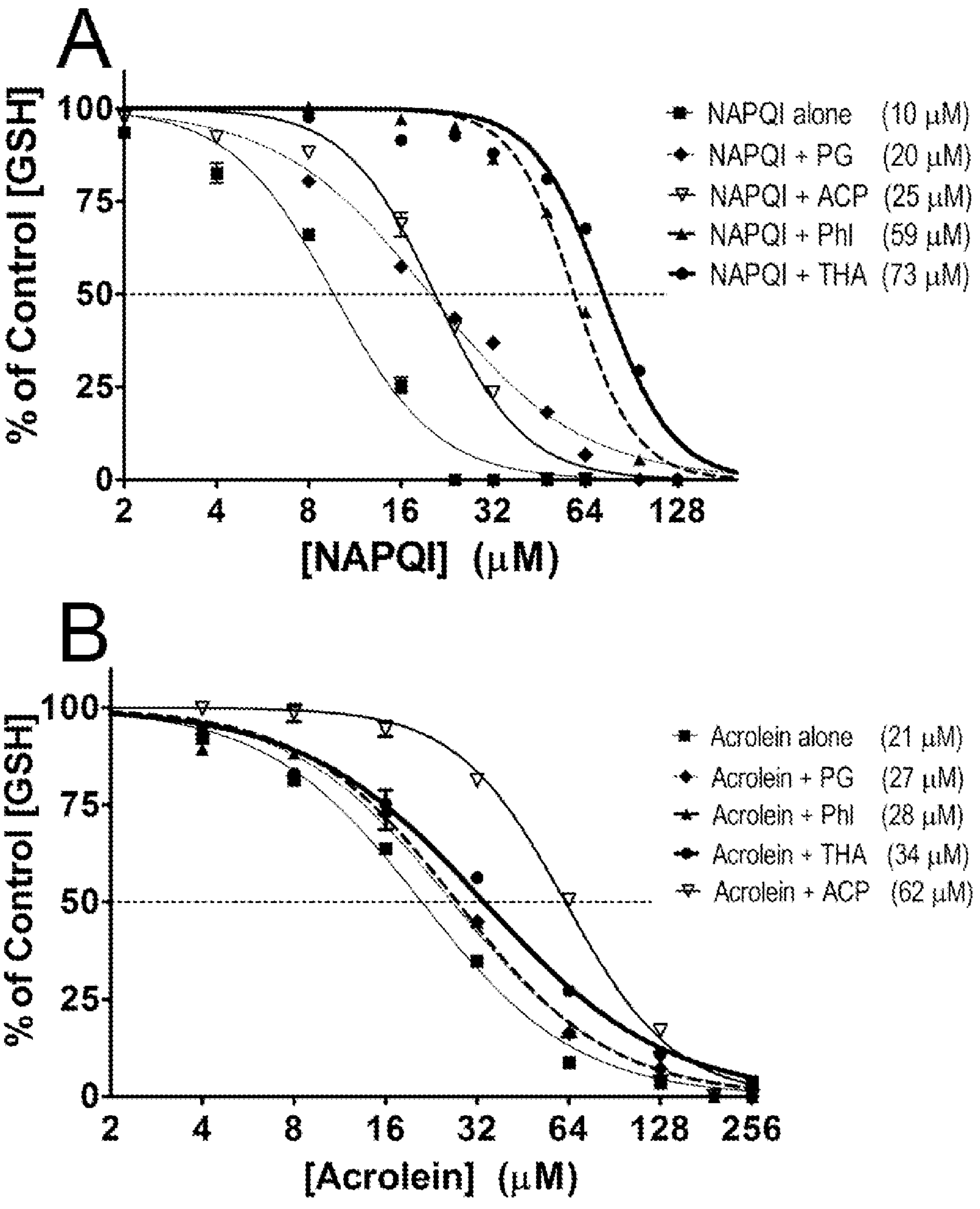
FIG. 2A-2B. Relative abilities of a nucleophile series to prevent NAPQI (A) or ACP (B) depletion of thiols (GSH). Calculated $IC_{50}$ values are provided in parentheses. PG=phloroglucinol; ACP=2-acetylcyclopentanone; Phl=phloretin; THA=2',4',6'-trihydroxyacetophenone.

Our research indicated that phloretin was a poor drug candidate due to significant toxicity. However, studies defining structure-activity relationships (SAR) for the phloretin molecule identified two relevant pharmacophores (structural components related to pharmacological activity); i.e., 2',4',6'-trihydroxyacetophenone (THA) and 1,3,5,-trihydroxybenzene (phloroglucinol; Rezk et al., 2002) (FIG. 1). Both pharmacophores are relatively non-toxic (PG oral $LD_{50}$ mice=4.55 gm/kg; THA oral $LD_{50}$ mice=3.20 gm/kg) and, although research investigating THA is limited, in chemico and cell culture studies indicated that these compounds can trap free radicals and limit lipid peroxidation (Bentes et al., 2011; Kim and Kim, 2010; Kim et al., 2012; Mathiesen et al., 1997; Rezk et al., 2002; So and Cho, 2014). THA (but not PG) can form bidentate complexes with metal ions involved in the Fenton reaction (Mammino, 2013; Zhu et al., 2012) and both compounds are nucleophiles with similar nucleophilic reactivities ($\omega^-$, Table 1; see LoPachin et al., 2012 for detailed discussion). As nucleophiles, THA and PG can potentially scavenge toxic electrophiles that mediate oxidative stress (see ahead). However, these compounds differ significantly with respect to $pK_a$ values (Table 1). The relatively high $pK_a$ of phloroglucinol (PG; 8.45) indicates that at physiological pH, 7% will be in the carbanion state. This low concentration of the nucleophile limits electrophile scavenging and therefore relative cytoprotective ability. In contrast, the more acidic THA ($pK_a$=7.75) is approximately 33% ionized to the cytoprotective nucleophilic state at cellular pH. The importance of $pK_a$ to cytoprotection is illustrated in an in chemico study (FIG. 2) that differentiated the relative abilities of nucleophiles to prevent thiol (GSH) depletion by N-acetyl-p-quinone imine (NAPQI; the electrophilic metabolite of acetaminophen) or acrolein (unsaturated aldehyde product of oxidative stress). Results indicated that, regardless of electrophile, THA provided better thiol protection than PG. This finding is clearly related to differences in $pK_a$, since the respective nucleophilic values ($\omega^-$) were comparable (Table 1). Also noted in this study were the differential abilities of THA and 2-ACP to scavenge electrophiles; i.e., THA provided better protection against NAPQI-induced GSH loss (FIG. 2A), whereas 2-ACP was more effective against acrolein (FIG. 2B). Although both THA and 2-ACP have similar $pK_a$ values, 2-ACP is a better nucleophile based on HSAB calculations (Table 1). This, however, is inconsistent with the expectation that 2-ACP should be able to prevent GSH loss regardless of electrophile. Therefore, the noted in chemico differences in protective potencies are likely due to other factors that affect the rate of adduct formation. For example, the superior ability of THA to scavenge NAPQI relative to 2-ACP (FIG. 2B) might be due to lack of steric hindrance during adduct formation. The importance of steric factors in covalent adduct reactions related to cytoprotection has been recognized (LoPachin and Gavin, 2014) and, in this regard, the enolate of 2-ACP contains a non-planar five member ring, whereas enolates formed from phloretin, THA and PG, are planar ring structures (FIG. 1) that are less likely to be hindered in a reaction with NAPQI. It is noteworthy that, consistent with corresponding higher nucleophilicity (Table 1), 2-ACP provides better GSH protection from acrolein than THA or PG (FIG. 2B). As a small, three carbon electrophile, acrolein would be less constrained in a reaction with 2-ACP. The differences in respective adduct chemistries might indicate different clinical applications. Thus, THA might be more useful in treating drug-induced toxicities associated with potentially hindered electrophiles (see THA-electrophile sequence of FIG. 2A). In contrast, 2-ACP might be more effective treatment for pathogenic conditions associated with oxidative stress, where less hindered unsaturated aldehydes such as acrolein and 4-hydroxy-2-nonenal are involved (see 2-ACP-electrophile sequence of FIG. 2B).

TABLE 1

Nucleophilicity ($\omega^-$) and $pK_a$ values for phloretin and corresponding pharmacophores.

| Anion | Softness ($\sigma \times 10^{-3}$ $ev^{-1}$) | Nucleophilicity with NAPQI ($\omega^- \times 10^{-3}$ ev) | Nucleophilicity with Acrolein ($\omega^- \times 10^{-3}$ ev) | pKa | % Anion (pH 7.4) |
|---|---|---|---|---|---|
| 2-ACP | 418 | 485 | 204 | 7.8 | 28.0 |
| NAC | 367 | 667 | 316 | 9.5 | 0.80 |
| Phloretin | 494 | 285 | 105 | 7.3 | 55.0 |
| PG | 540 | 366 | 133 | 8.5 | 7.40 |
| THA | 485 | 325 | 114 | 7.7 | 33.0 |

Nucleophilicity ($\omega^-$) was calculated using Hard and Soft, Acids and Bases (HSAB) parameters according to method described in LoPachin and Gavin, 2014. $\omega^-$ values were calculated individual reacting electrophiles: NAPQI and acrolein.

Although THA has physicochemical properties consistent with cytoprotection, the majority of published research has focused on PG pharmacology and its potential clinical applications (reviewed in Singh and Bharate, 2006); e.g., prevention of ionizing radiation damage (Piao et al., 2014), antiplatelet effect and treatment of atherosclerosis (Chang et al., 2012) and attenuation of neurodegenerative conditions (Ryu et al., 2013). A combination of PG and trimethylphloroglucinol (Spasfon™, Cephalon, France) is used in the treatment of irritable bowel syndrome and other spastic conditions (Chassany et al., 2007). Furthermore, a PG derivative, hyperforin, is the primary pharmacological component of St. John's Wort, which is used in the treatment of depression and migraine headaches (Wurglics and Schubert-Zsilavecz, 2006; Zanoli, 2004). Growing experimental evidence also indicates that PG slows the progression of β-amyloid neurotoxicity and memory deficits in transgenic mouse models of Alzheimer's disease (AD; Brenn et al., 2014; Dinamarca et al., 2006; Griffith et al., 2010). This suggests that PG or a derivative could be developed as a treatment for neurodegenerative diseases. This diversity of effects and potential medical uses has generated a significant number of patents (Singh et al., 2009).

THA Cytoprotection

Figure 3A:
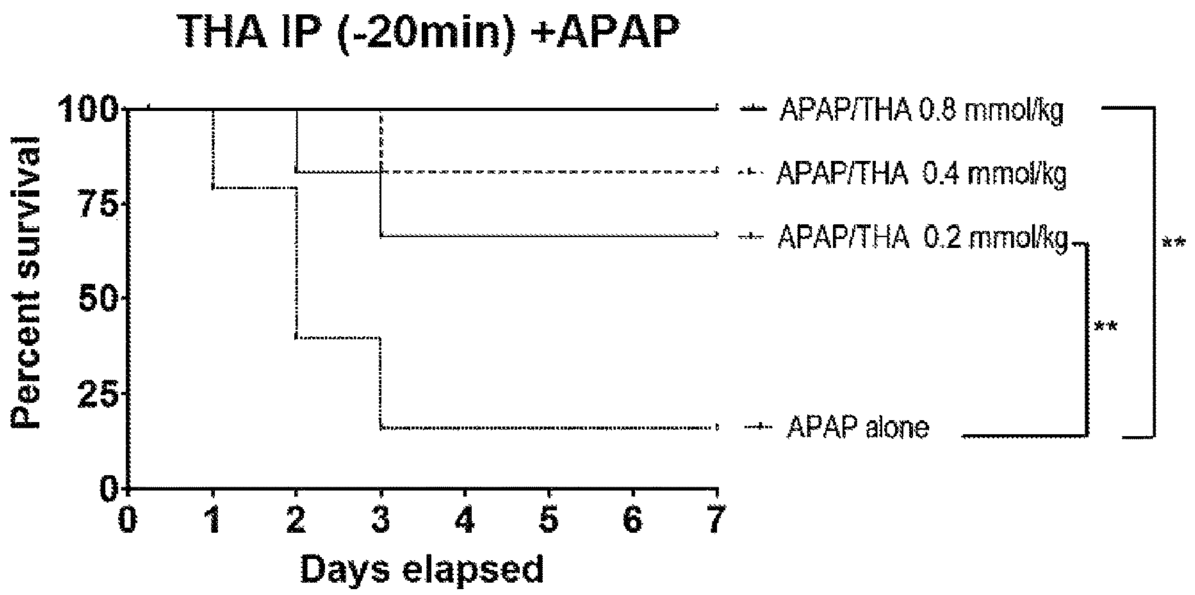
FIG. 3A-3B. Survival curves, THA and PG i.p. administration. A. Survival curves showing dose-dependent effects of THA administered i.p. 20 mins prior to APAP. No lethality was associated with these doses. B. Survival curves showing dose-dependent effects of PG administered i.p. 20 mins prior to APAP. No lethality was associated with these doses. Joining lines at right side of figure indicate statistically significant differences in treatment groups at *$P<0.001$ and $P<0.01$ levels of significance.
Figure 3B:
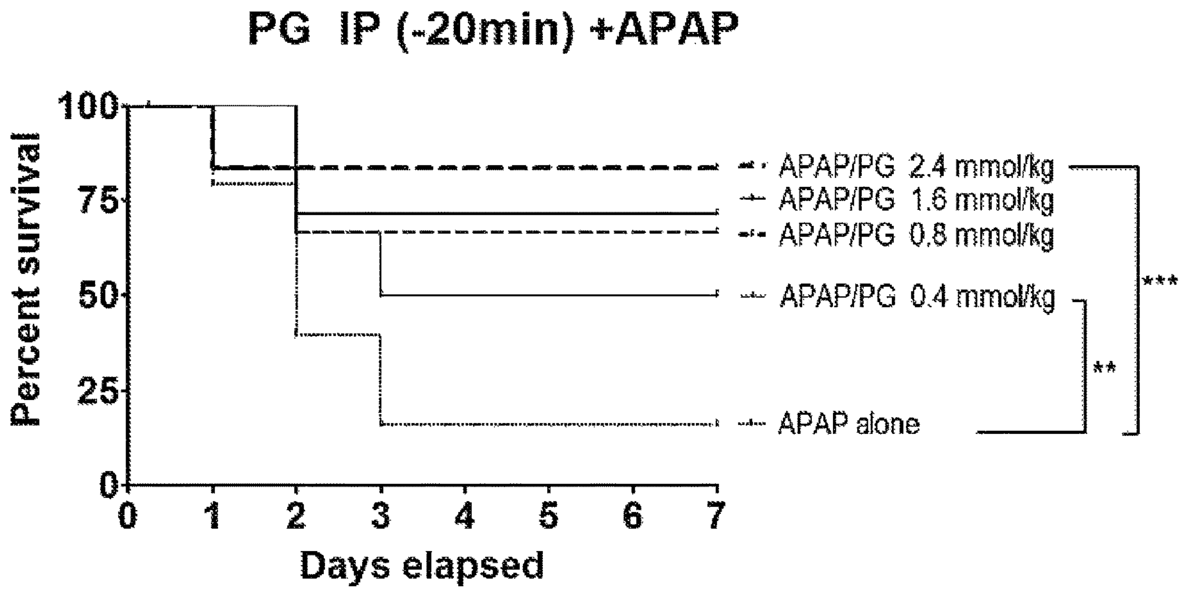
Figure 4A:
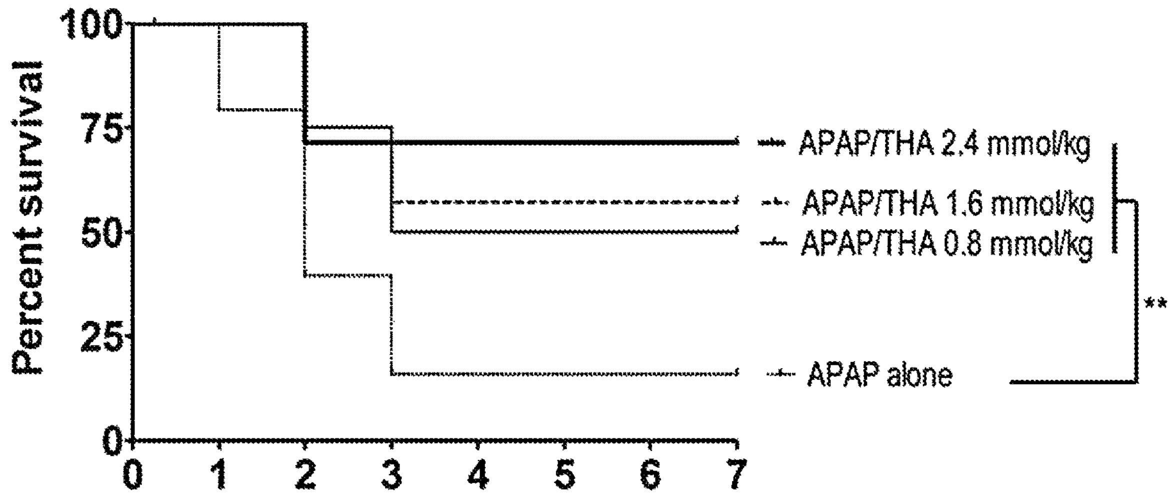
FIG. 4A-4B. Survival curves, THA and PG oral administration. A. THA given orally (0.8-2.40 mmol/kg) provided dose-dependent protection against APAP hepatotoxicity. B. Oral PG was ineffective over a broad dose-range (0.8-2.40 mmol/kg). Joining line indicates statistically significant differences in treatment groups at **$P<0.01$ level of significance.
Figure 4B:
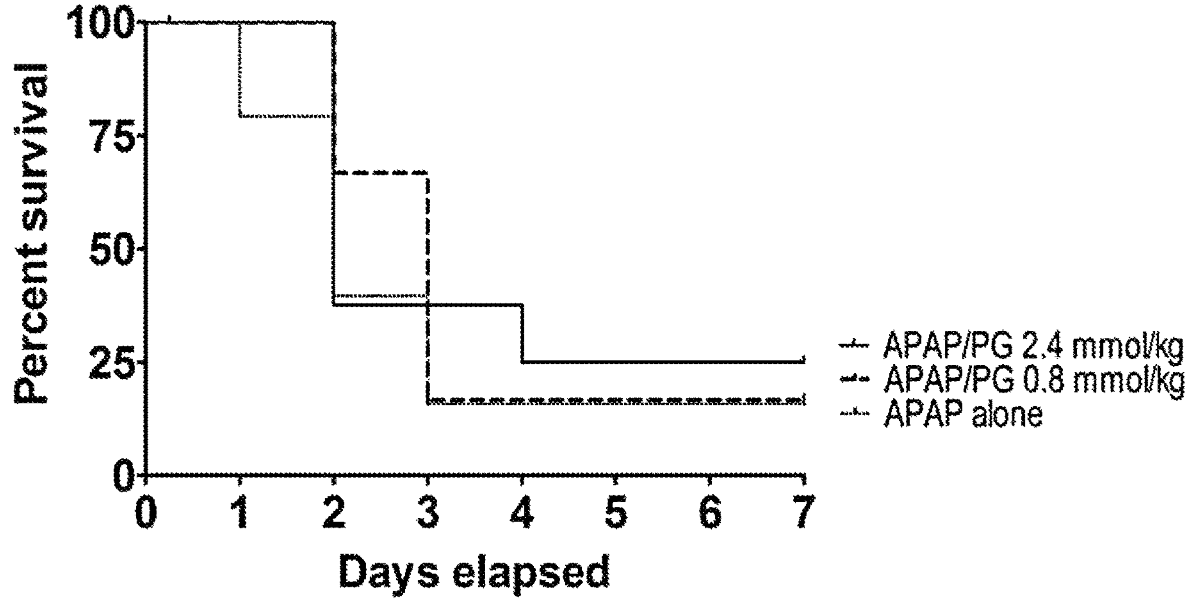

As indicated above, THA has received almost no attention as a possible cytoprotectant; a single publication (Ferreira et al., 2010) showed that THA (0.032 mmol/kg, po) could completely prevent carbon tetrachloride (0.5 ml/kg; ip)-induced hepatotoxicity in mice. Nonetheless, the physicochemical characteristics of THA implicate cytoprotection (see above) and therefore this compound was tested in an animal model of oxidative stress: APAP overdose in mice. Results (FIG. 3A) indicate that THA administered i.p. produced dose-dependent (0.20-0.80 mmol/kg) hepatoprotection in APAP-intoxicated mice. PG was also protective (i.p.) in this model (FIG. 3B), although at a higher dose-range (0.40-2.40 mmol/kg). Administration of either pharmacophore at the highest effective dose did not produce toxicity or lethality over a 7 day observation period (data not shown). Oral THA (FIG. 4A) also produced dose-dependent hepatoprotection, whereas similar administration of PG (FIG. 4B) was completely ineffective over a broad dose range (0.80-2.40 mmol/kg).

NAHA Cytoprotection

Figure 5A:
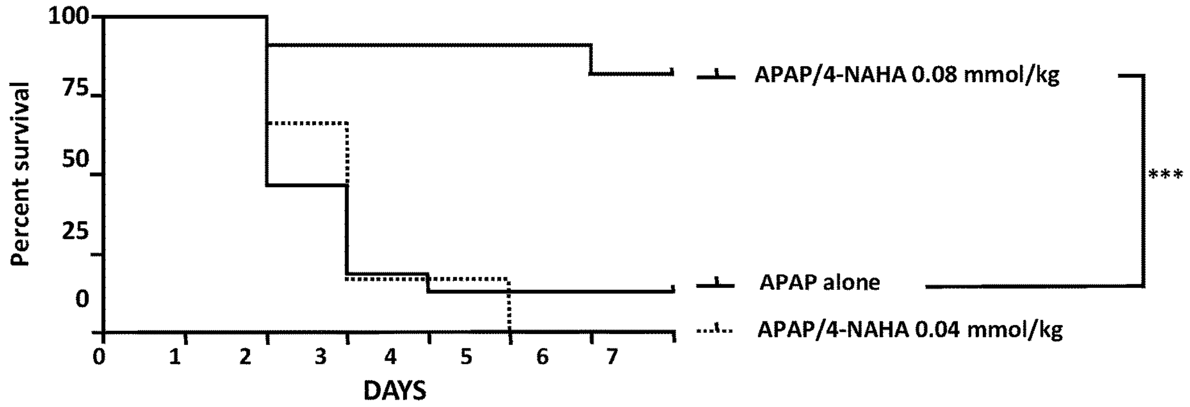
FIG. 5A-5B. Survival curves, 4-NAHA i.p. and oral administration. A. 4-NAHA given i.p. (0.04-0.08 mmol/kg) provided dose-dependent protection against APAP hepatotoxicity. B. Oral 4-NAHA was effective over a broader dose-range (0.04-0.12 mmol/kg). Joining lines indicate statistically significant differences in treatment groups at *$P<0.001$ and $P<0.01$ levels of significance.
Figure 5B:
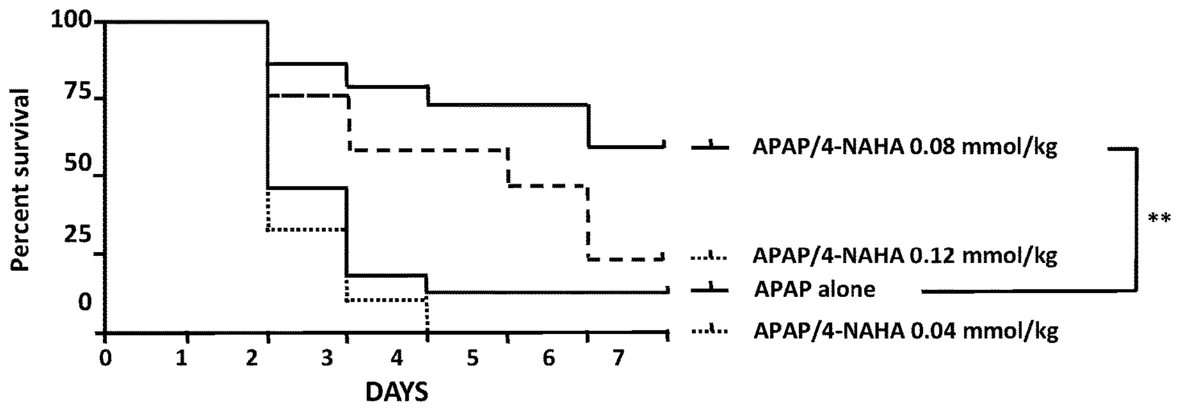

A THA derivative, 4-acetyl-2,6-dihydroxy acetophenone (4-NAHA) (FIG. 1) was also tested in the APAP mouse model. Administration of 4-NAHA i.p. at 0.04 mmol/kg was ineffective, whereas 0.08 mmol/kg produced significant hepatoprotection (FIG. 5A). When administered orally, 0.12 mmol/kg oral dose was partially protective; i.e., lethality was significantly delayed, whereas the 0.04 mmol/kg dose was ineffective (FIG. 5B). These NAHA doses were not acutely toxic and all doses tested did not cause delayed toxicity (7 days).

N-Acetyl Cysteine (NAC) Cytoprotection

Figure 6:
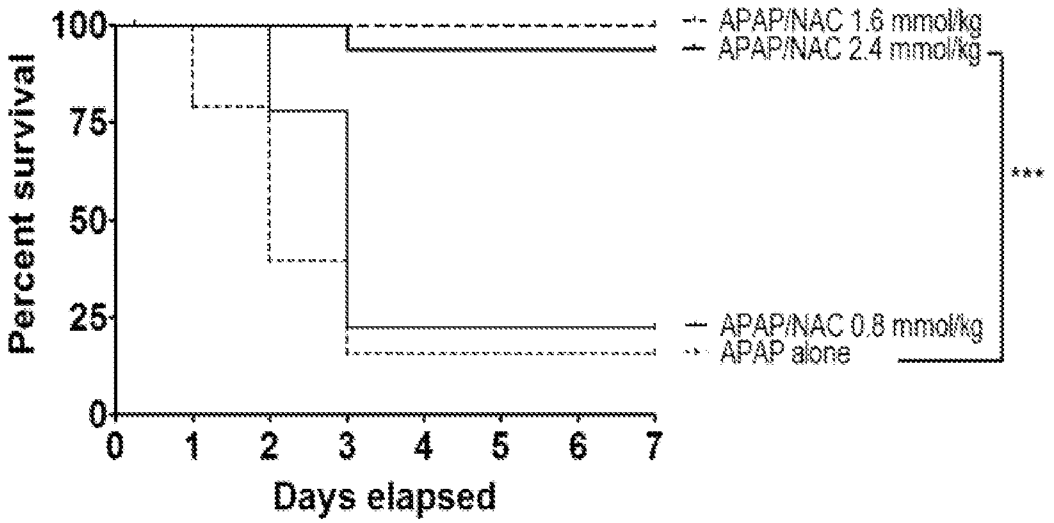
FIG. 6. Survival curves showing dose-dependent effects of NAC administered oral 20 mins prior to APAP. Joining line indicates statistically significant differences in treatment groups at ***$P<0.001$ level of significance.

N-acetyl cysteine (NAC; Mucomyst®), the approved clinical treatment for APAP overdose, was an effective APAP antidote only when administered orally and at a higher dose-range (1.60-2.40 mmol/kg; FIG. 6). These data show that regardless of route, THA and NAHA can prevent APAP hepatotoxicity at low μmol doses. It is possible that hepatoprotection involves inhibition of APAP bioactivation (Jaeschke et al., 2012). However, Zhang et al. (2013) provided evidence that APAP metabolism was not disrupted in 1,3-dicarbonyl pretreated mice since early transient APAP-induced changes in liver injury biomarkers (e.g., hepatocyte unsaturated aldehyde content) were evident indicating NAPQI generation and subsequent toxicological effects.

Figure 7:
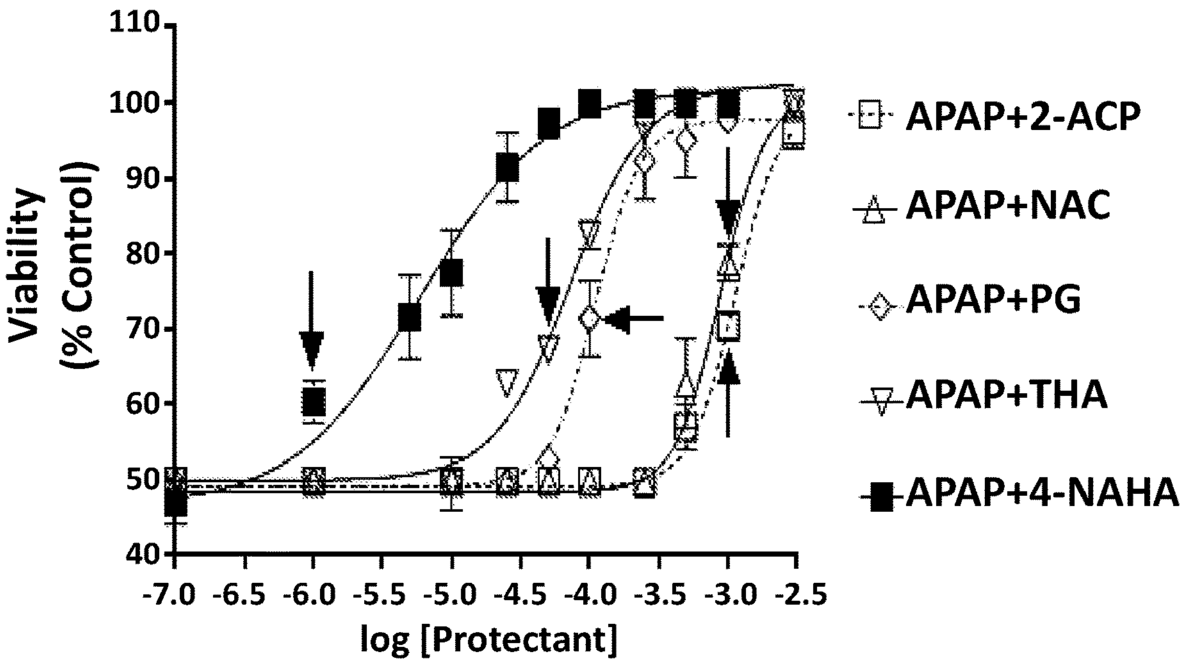
FIG. 7. Effects of graded protectant concentrations (0.010-5.0 mM) on viability of APAP-exposed (1.0 mM×4 hrs) mouse hepatocytes. Arrows indicate the first cytorprotectant concentration at which the mean viability data are significantly different from the APAP-alone data.

Hepatoprotection in an Isolated Mouse Hepatocyte Model of Acetaminophen Toxicity The respective efficacies and potencies of individual cytoprotectants (THA, PG, NAHA, 2-ACP and NAC) were determined in APAP-exposed isolated mouse liver cells (hepatocytes). Hepatocytes were exposed to APAP (1.0 mM) and incubated (4 hrs) with graded concentrations (0.010-5.0 mM) of putative protectant (FIG. 7). Results indicated that exposure of hepatocytes to APAP (1.0 mM×4 hrs) caused a decrease in mean (±SEM) cell viability of 52±7%. All compounds tested provided concentration-dependent protection of equivalent efficacy (maximum cytoprotective effect), but dissimilar potency. As evidenced by the respective concentration profiles (FIG. 7), THA and PG were substantially more potent than either 2-ACP or NAC; e.g., $EC_{50}$ THA/PG=~90 μM vs $EC_{50}$ 2-ACP/NAC=~1.0 mM. However, NAHA was the most potent cytoprotectant tested; i.e., $EC_{50}$=6.0 μM.

Concentration-Response Analysis: Variable APAP

Figure 8A:
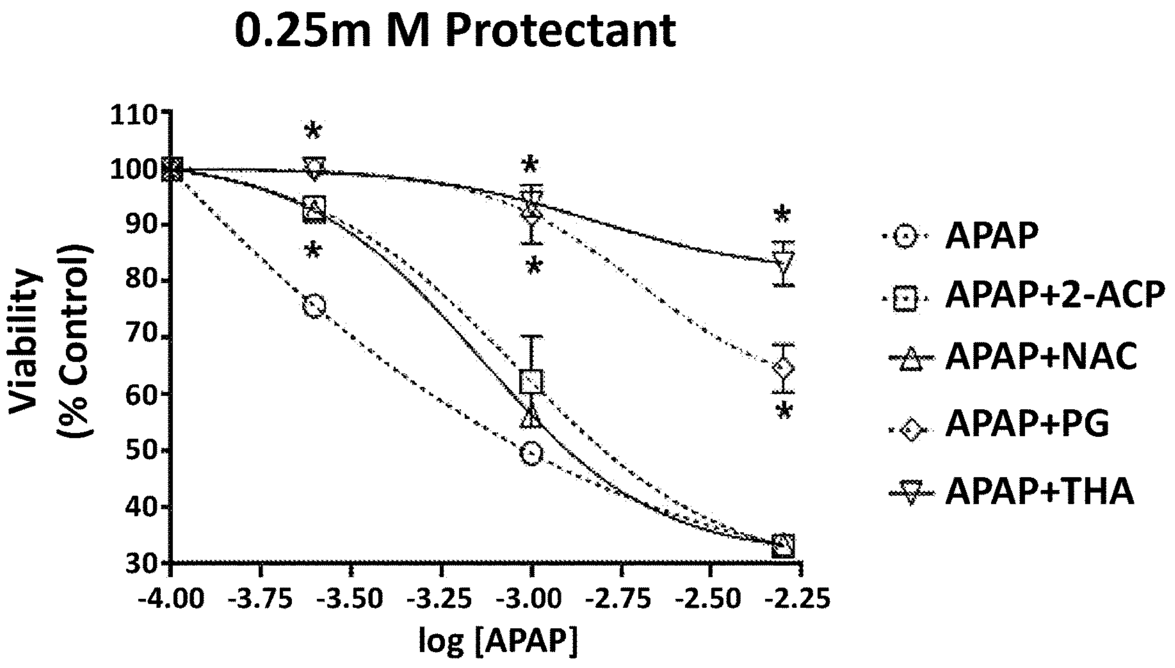
FIG. 8A-8B. Effects of 0.25 mM (A) or 1.0 mM (B) protectant on viability of hepatocytes exposed to graded APAP concentrations (0.25-5.0 mM×4 hrs). Data are expressed as mean percent of control±SEM and *indicates $p<0.05$.
Figure 8B:
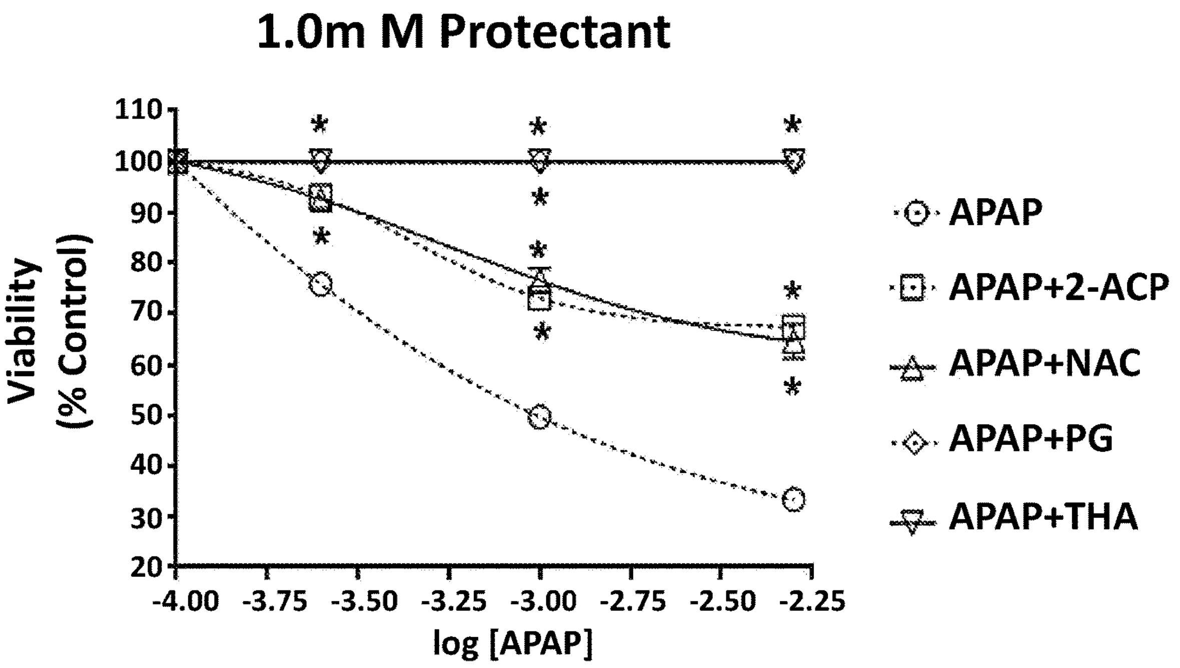
Figures 9A, 9B, 9C, 9D:
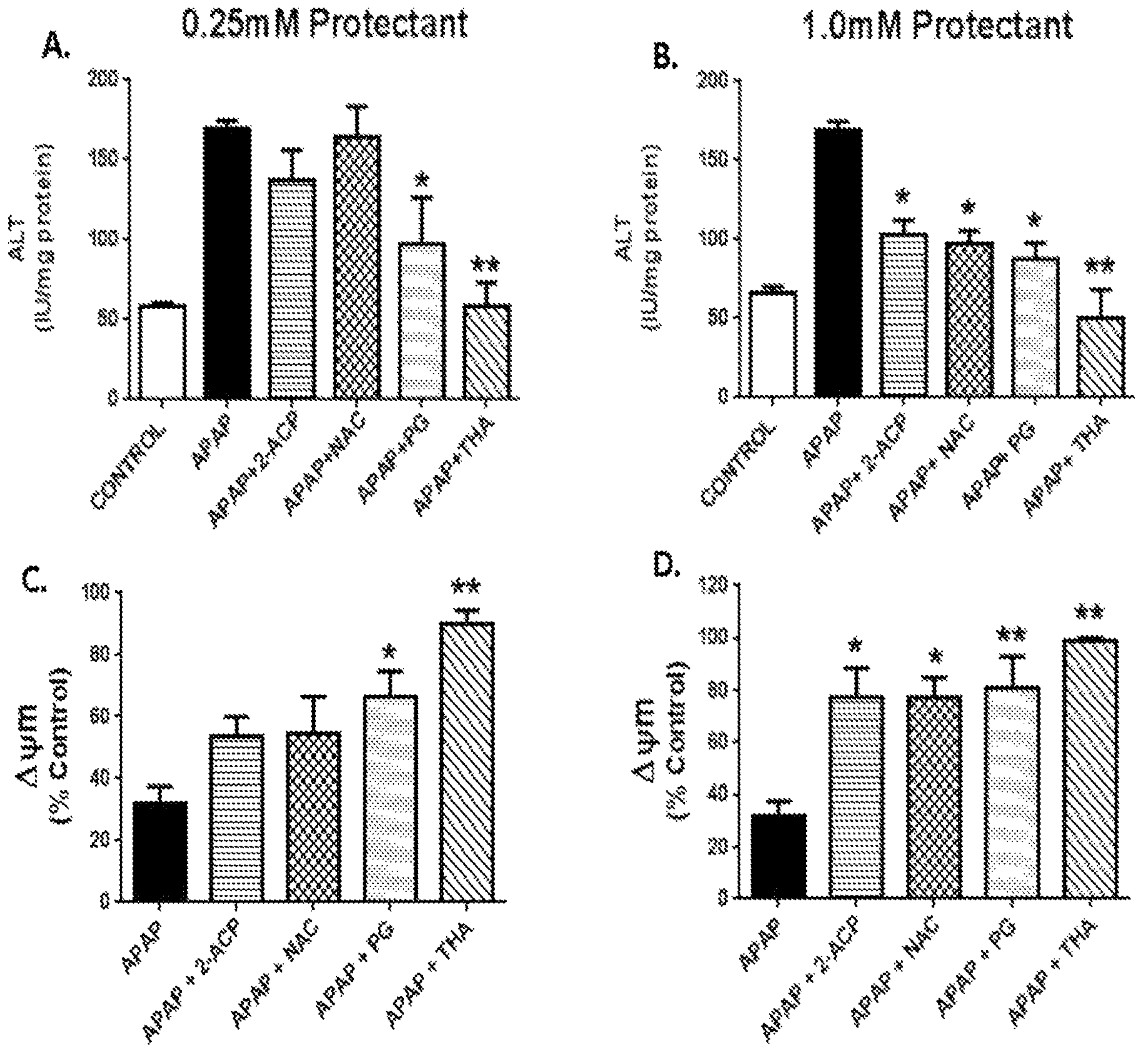
FIG. 9A-9D. This figure is a continuation of analyses presented in FIG. 8. Described are the respective effects of 0.25 mM or 1.0 mM protectant on ALT appearance (A and B) and changes in mitochondrial membrane potential (Δψm; C and D) in isolated mouse hepatocytes exposed to APAP (1.0 mM×4 hrs). *$P<0.05$, **$P<0.01$ levels of statistical significance.

To obtain a more complete definition of cytoprotective pharmacology, isolated hepatocytes were exposed to protectant (either 0.25 or 1.0 mM) and graded concentrations of APAP (0.25-5.0 mM×4 hrs). Results show that APAP exposure caused progressive concentration-dependent loss of hepatocyte viability (FIG. 8) that was associated with substantial derangement of both hepatocyte enzyme concentrations (ALT, AST and LDH) in media and mitochondrial membrane potential (FIG. 9). At a lower cytoprotectant concentration (0.25 mM; FIG. 8A), neither 2-ACP nor NAC provided cytoprotection beyond the lowest APAP concentration (0.25 mM). In contrast, both THA and PG were fully protective up to the 1.0 mM APAP concentration (FIG. 8B). This differential cytoprotection among the compounds tested is reflected in the corresponding changes in the toxicity indices (FIG. 9). At the highest APAP concentration (5.0 mM), THA (0.25 mM) preserved cell viability, whereas PG (0.25 mM) provided only partial cytoprotection as evidenced by significantly reduced cell viability (FIG. 8A) and corresponding changes in toxicity parameters (FIGS. 9A and 9C). These data are consistent with the previous rank order of concentration dependent cytoprotection (FIG. 7). When the concentration of cytoprotectant was increased to 1.0 mM (FIG. 8B), THA or PG provided full hepatocyte protection irrespective of APAP concentration. Protection was characterized by normal (THA) to near-normal (PG) toxicity measures (FIGS. 9B and 9D). When APAP-exposed hepatocytes were incubated with either 2-ACP or NAC at 1.0 mM, the partial cytoprotection provided (FIG. 8B) was accompanied by a return toward normalization of the toxicity indices (FIGS. 9B and 9D).

Figure 10:
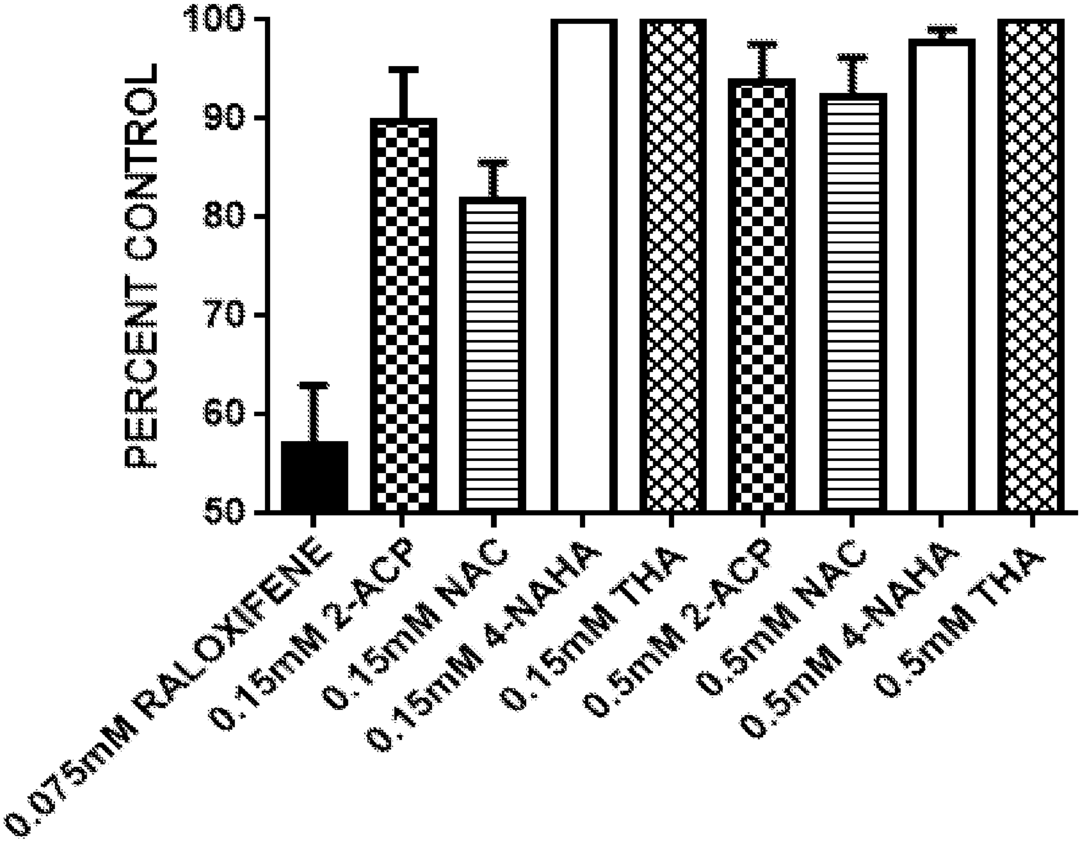
FIG. 10. Prevention of raloxifene-induced hepatocyte toxicity. This figure shows the relative abilities of dicarbonyl (2-ACP), thiol (NAC) and polyphenol (4-NAHA, THA) compounds to prevent raloxifene-induced hepatocyte toxicity. The data show that THA and 4-NAHA provide superior protection in this model of drug-induced toxicity.

In addition to the APAP model of hepatoprotection, studies were initiated of other drug-induced toxicities. For example, raloxifene (Evista®) is a selective estrogen receptor modulator used in the prevention of post-menopausal osteoporosis. It is metabolized by CYP3A4 to a toxic quinone electrophile (Chen et al., 2002). FIG. 10 shows that raloxifene exposure produced hepatocyte toxicity at relatively low concentrations (75 μM). Although 2-ACP and NAC provided partial protection against raloxifene at 150 both 4-NAHA and THA were fully protective. All tested nucleophiles were fully protective at the higher concentration (500 μM; FIG. 10). These data provide initial evidence that the dicarbonyl/polyphenol compounds might be useful in a variety of drug-induced toxicities.

Hepatocyte Rescue

Figure 11A:
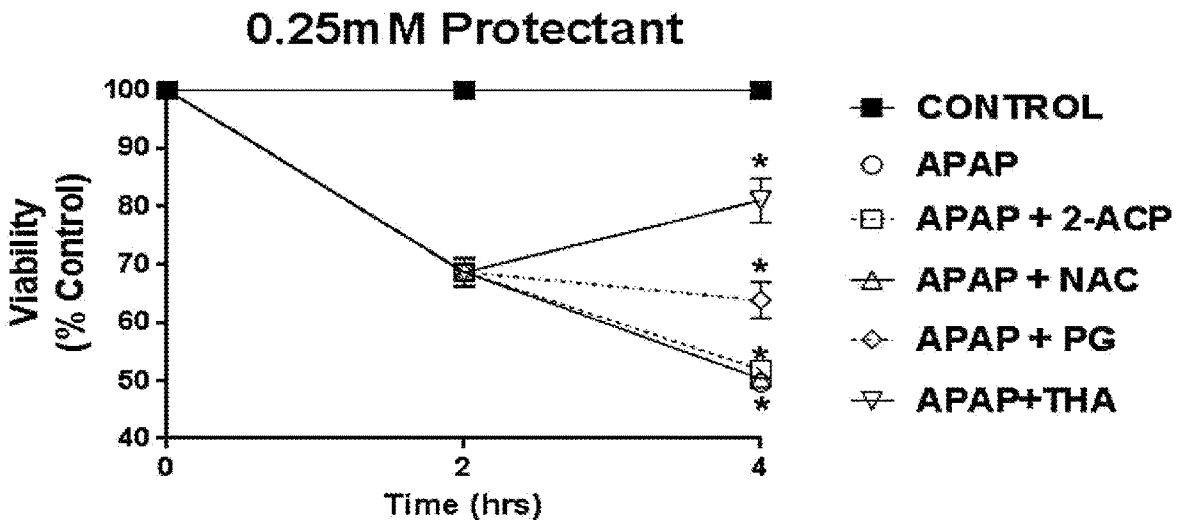
FIG. 11A-11C. Effects of graded cytoprotectants concentrations (0.25-5.0 mM (A-C)) on temporal loss of viability induced by APAP exposure (1.0 mM). After 2 hrs of APAP incubation, protectant was added and viability was determined after additional 2 hrs. *$P<0.05$ levels of statistical significance.
Figure 11B:
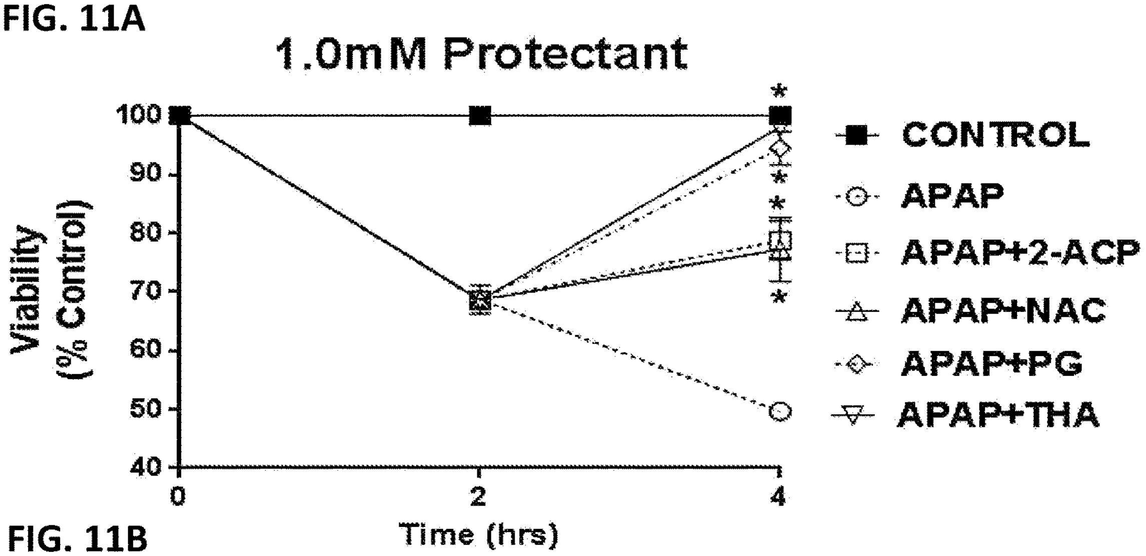
Figure 11C:
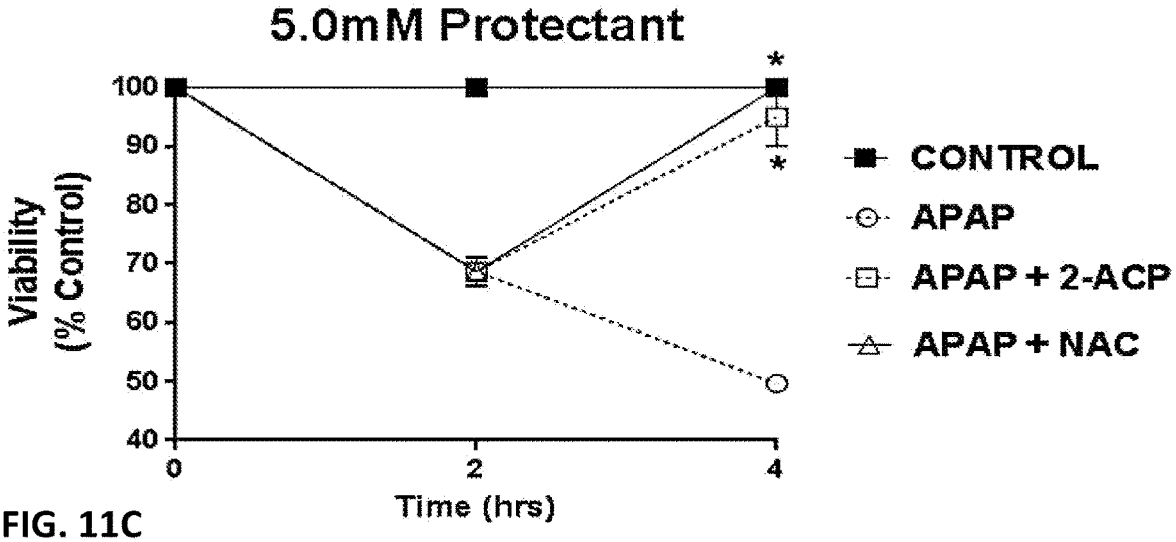
Figures 12A, 12B, 12C, 12D, 12E, 12F:
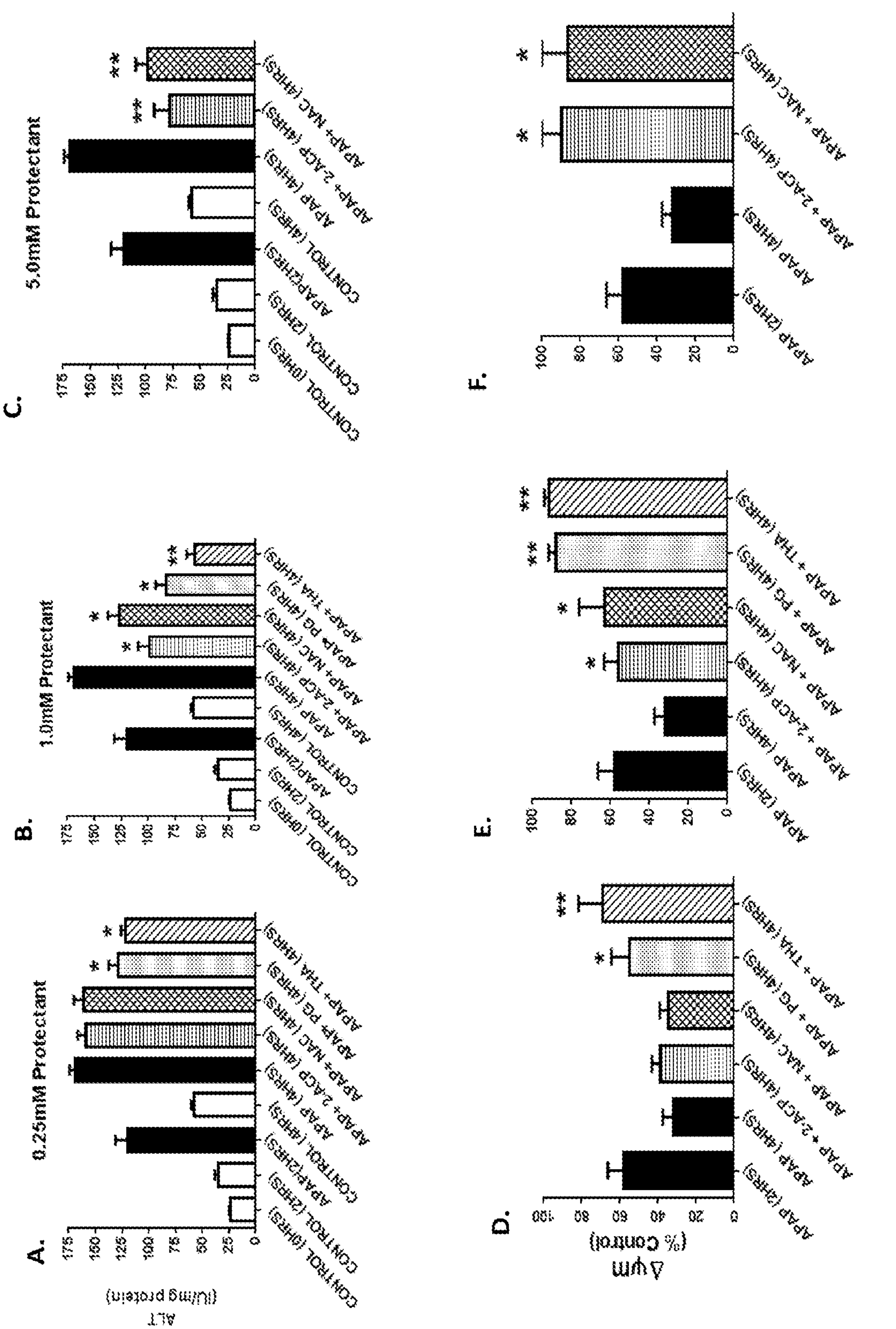
FIG. 12A-12F. This figure is a continuation of analyses presented in FIG. 11. Described are the respective effects of 0.25, 1.0 or 5.0 mM protectant on ALT appearance (A-C) and changes in mitochondrial membrane potential (Δψm; D-F) in isolated mouse hepatocytes exposed to APAP (1.0 mM×4 hrs). Parameters were measured at 4 hrs after APAP exposure as per FIG. 9. *$P<0.05$, **$1^3<0.01$ levels of statistical significance.

The relative abilities of the cytoprotectants to arrest or otherwise modify the ongoing development of APAP hepatocyte toxicity were determined. After an initial 2 hrs of incubation with APAP (1.0 mM) alone there was a 31.5±7.0% reduction in mean (±SEM) cell viability (FIG. 11) associated with increases in the media content of hepatocyte enzymes (FIG. 12A-C) and depolarization of mitochondrial membranes (FIG. 12D-F). Hepatocyte toxicity continued to progress over an additional 2 hrs of APAP incubation; i.e., mean cell viability decreased to 49.5±9.0% after 4 hrs (total) of incubation (FIG. 11). This loss of viability was associated with further derangement of the toxicity parameters (FIG. 12). However, addition of cytoprotectant 2 hrs post-APAP exposure modified subsequent progression of cytotoxicity in a concentration-dependent manner. Thus, although 2-ACP and NAC were ineffective at the lowest concentration tested (0.25 mM; FIG. 11A), both compounds truncated the rapid decline in viability at 1.0 mM (FIG. 11B). At 5 mM (FIG. 11C), 2-ACP and NAC promoted recovery of APAP-exposed hepatocytes. The concentration-dependent restoration of cell viability mediated by 2-ACP and NAC was correlated with significant improvements in corresponding toxicity indices (FIG. 12). THA provided partial recovery of viability at the lowest concentration (0.25 mM; FIG. 11A), whereas PG arrested the progression of APAP-induced toxicity (FIG. 12A). At the 1.0 mM concentration, PG and THA promoted complete restoration of viability in APAP-exposed hepatocytes (FIG. 11B). The return to control viability was accompanied by normalization of the toxicity indices (FIG. 12). The observed changes in hepatocyte viability were confirmed by parallel measurements of the liver-specific enzymes in the incubation medium: aspartate aminotransferase (ALT) and alanine aminotransferase (AST; data not shown). In addition, lactate dehydrogenase (LDH) activity was measured as a determinant of general cell injury (data not shown).

These results demonstrate that 1,3-dicarbonyl compounds can provide cytoprotection in an isolated cell model of APAP hepatotoxicity. Because pharmacokinetics is not an issue, these findings in isolated hepatocytes indicate that protection in animal models (FIGS. 3-5) is not due to dicarbonyl-altered APAP tissue distribution. Alternatively, it is possible that hepatoprotection involves inhibition of APAP bioactivation (Jaeschke et al., 2012). However, the ability of PG and THA to rescue APAP-exposed cells (FIG. 11) provides evidence that cytoprotection is not a function of inhibited cytochrome P450 (2E1) conversion of APAP to the toxic NAPQI metabolite. Moreover, Zhang et al. (2013) provided evidence that APAP metabolism was not disrupted in 1,3-dicarbonyl pretreated mice. Specifically, early transient APAP-induced changes in liver injury biomarkers (e.g., hepatocyte unsaturated aldehyde content) were evident indicating NAPQI generation and subsequent toxicological effects. Instead, mechanism studies (LoPachin et al., 2011), in conjunction with the in chemico experiments (FIG. 2) and supporting HSAB analyses (Table 1), indicate that physicochemical attributes of the enolate such as nucleophilic reactivity ($\omega^-$), acidity (indicated by $pK_a$ values) and metal ion chelation are directly involved in cytoprotection.

Conclusions

The present animal and isolated hepatocyte studies indicate that THA and NAHA provide substantial cytoprotection in APAP toxicity. Substantial evidence suggests that this protection involves their ability to block the oxidative stress cascade at several steps. THA is a nucleophile that can scavenge electrophiles such as NAPQI (the toxic APAP metabolite; FIG. 2A) and the unsaturated aldehydes that mediate secondary oxidative stress. In addition, THA can trap free radicals that initiate oxidative stress and can chelate metal ions that participate in the free radical generating Fenton reaction. In contrast, PG was less effective than THA with respect to reducing APAP hepatotoxicity in mice, which could be directly related to the inability to chelate metal ions and to scavenge electrophiles such as NAPQI (FIG. 2). Based on the respective physicochemical and pharmacological attributes, THA and NAHA are substantially more potent cytoprotectants than PG and are therefore likely to have more extensive clinical utility.

The efficacy and potency demonstrated in the present studies, in conjunction with favorable pharmacokinetics, suggest that 4-NAHA and THA (and analogues) could be co-formulated with Tylenol® as an "on-board" protectant. This is an unprecedented concept and therefore represents a new, innovative approach to the pharmacological management of pain and inflammation. The re-formulation of Tylenol® will provide a hepatoprotectant that would prevent both accidental and intentional (suicide) overdose. This will reduce hospital costs related to liver transplantation and length-of-stay. In addition, the marketability of Tylenol® has been traditionally limited by the lack of anti-inflammatory actions. However, the anti-inflammatory properties of the added dicarbonyl/polyphenol compounds (e.g., see Sappington et al., 2005) will increase the corresponding clinical utility and permit the improved Tylenol® version to compete in the non-steroidal anti-inflammatory drug (NSAIDs) market. N-acetyl cysteine (NAC) would be less effective in this role since the cytoprotective mechanism does not involve direct electrophile (e.g., NAPQI) scavenging, which is necessary to truncate the onset of acute hepatotoxicity. The present findings support the enolate theory of cytoprotection (LoPachin et al., 2011, 2012) and provide convincing evidence that multifunctional enolate-forming compounds might represent a developmental platform for cytoprotectants that prevent drug-induced toxicity mediated by electrophilic metabolites. In this regard, Tylenol®-induced liver damage is only one example of high volume drugs that cause therapy-limiting toxicity mediated by metabolites; e.g., atorvastatin (Lipitor®) is metabolized to a highly toxic quinone immine metabolite. Reformulation of these drugs with a dicarbonyl/polyphenol derivative could prevent the associated drug-induced toxicities and thereby broaden the respective markets. The benefits of co-formulation could also apply to the resurrection of numerous effective drugs that have been removed from the market due to metabolite toxicity.

The present studies involve the identification of novel nucleophilic antioxidant compounds derived from a phyto-polyphenol and related compounds. This unique chemical species can reduce cell injury associated with oxidative stress through multiple cytoprotective mechanisms; i.e., by trapping free oxygen/nitrogen radicals, chelating metal ions that catalyze the Fenton reaction and scavenging unsaturated aldehyde electrophiles. Therefore, these compounds are expected to be useful in treating pathogenic conditions that have oxidative stress as a common molecular etiology; e.g., atherosclerosis, ischemia/reperfusion (FR) injury, diabetes, spinal cord injury and Alzheimer's disease. As a relatively strong nucleophile, these compounds can bind electrophilic toxicants and thereby prevent associated cytotoxicity. Therefore, these compounds are expected to be useful in treating toxicities due to, for example, administration of drugs that are electrophilic (e.g., cisplatin) or those that are transformed to a reactive electrophilic metabolite (e.g., acetaminophen). These compounds are also expected to be useful in treating diseases (e.g., atherosclerosis, diabetes) that can be accelerated by exposure to electrophilic environmental pollutants. Oxidative stress injury and electrophile toxicities are significant pathogenic factors that impact the quality of human health. These compounds are expected to mitigate these mechanisms and therefore have very broad pharmacotherapeutic implications.

Example B—Chemical Studies

Possible pathways for THA analogue synthesis:

a. The Bucherer Reaction followed by Friedel-Crafts Reaction (illustrated for $R^2$=$NH_2$):

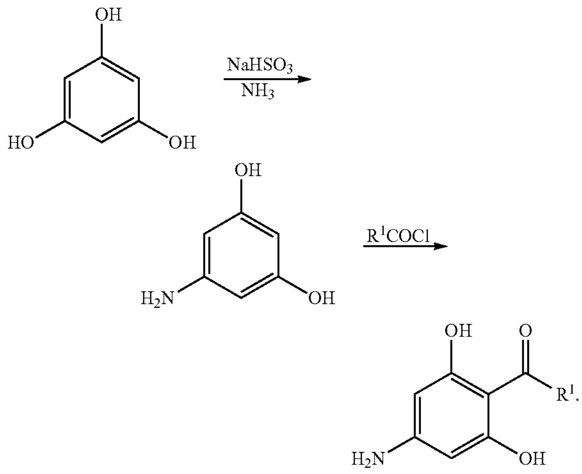

b. Alternatively, THA may be used as the starting material for the Bucherer Reaction (if $R^1$ analogues ketones are unavailable, the Friedel-Crafts reaction can be followed by the Bucherer Reaction).

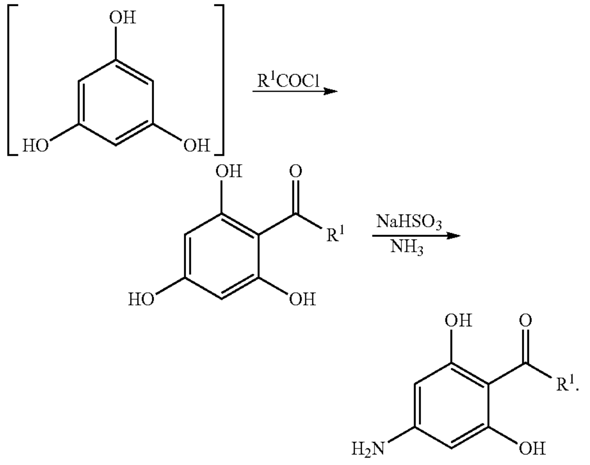

c. It may be necessary to protect the OH groups during some synthetic transformations; for example, the following compound may be used in place of phloroglucinol (R=H):

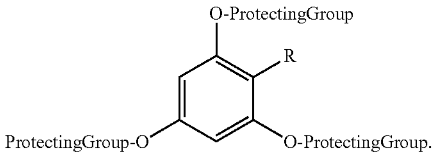

Computational Data on THA analogues:

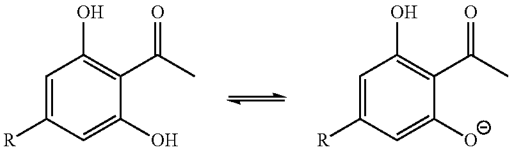

| R | ω- (x $10^{-3}$ ev) | $pK_a$ (* estimate) | % Anion (pH = 7.4) |
|---|---|---|---|
| 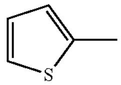 | 74 | | |
| $—CF_3$ | 78 | | |
| 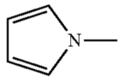 | 87 | | |
| $—OCOCH_3$ | 90 | | |
| —SH | 94 | 7.5* | 44 |
| $—NHCOCH_3$ | 97 | 7.3* | 56 |
| $—SCH_3$ | 98 | 7.5* | 44 |
| —F | 102 | | |
| 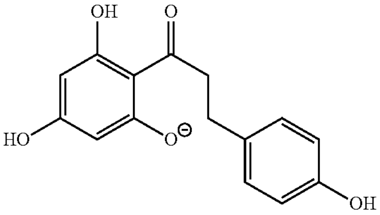 | 105 | 7.3 | 56 |
| —H | 107 | 7.8* | 28 |
| 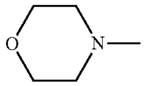 | 121 | | |
| 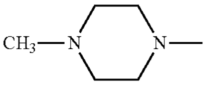 | 122 | 8.0* | 20 |
| —OH | 133 | 7.7 | 33 |
| 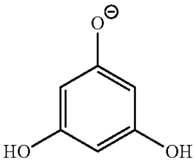 | 133 | 8.5 | 07 |
| 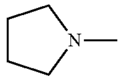 | 135 | | |
| $—NH_2$ | 144 | 8.0* | 20 |

REFERENCES

Chang M C, Chang H H, Chan C P, Chou H Y Chang B E, Yeung S Y, Wang T and Jeng J H (2012) Antiplatelet effect of phloroglucinol is related to inhibition of cyclooxygenase, reactive oxygen species, ERK/p38 signaling and thromboxane A2 production. *Toxicol App Pharmacol* 263: 287-295.

Chassany O, Bonaz B, Des Varannes B., Bueno L, Cargill G, Coffin B, Ducrotte P and Grange V. (2007) Acute exacerbation of pain in irritable bowel syndrome: efficacy of phloroglucinol/trimethyphloroglucinol—a randomized double-blind, placebo-controlled study. *Aliment Pharmacol.* 25: 1115-1123.

Chen Q, Ngui J S, Doss G A, Wang R W Cai X, DiNinno F P, Blizzard T A, Hammond M L, Stearns R A, Evans D C, Gaillie T A and Tang W. (2002) Cytochrome P450 3A4-mediated bioactivation of raloxifene: Irreversible enzyme inhibition and thiol adduct formation. Chem Res Toxicol 15: 907-914.

Bentes A L A, Borges R S, Monteiro W R, de Macedo L G M and Alves C N (2011) Structure of dihydrochalcones and related derivatives and their scavenging and antioxidant activity against oxygen and nitrogen radical species. *Molecules* 16: 1749-1760.

Brenn A, Grube M, Jeditschky G., Fischer A, Strohmeier B, Eiden M, Kell M, Groschup M H and Vogelgesang S. (2014) St. John's Wort reduces beta-amyloid accumulation in a double transgenic Alzheimer's disease mouse model-role of P-glycoprotein. *Brain Pathol* 24: 1824. Epub 2013 Jun. 28.

Dinamarca M C, Cerpa W, Garrido J, Hancke J L and Inestrosa N C (2006) Hyperforin prevents β-amyloid neurotoxicity and spatial memory impairments by disaggregation of Alzheimer's amyloid-β-deposits. *Mole Physch.* 11: 1032-1048.

Ferreira E A, Gris E F, Felipe K B, Correia J F G, Cargnin-Ferreira E, Filho D W and Pedrosa C. (2010) Potent hepatoprotective effect in CC14-induced hepatic injury in mice of phloroacetophenone from *Myrcia multiflora. Libyan J Med* 5: 4891-4896.

Galati F and O'Bien P J (2004) Potential toxicity of flavonoids and other dietary phenolics: significance for the chemopreventive and anticancer properties. *Free Rad. Biol. Med* 37: 287-303.

Geohagen, B., Vydyanathan, A., Kosharskyy, B., Shaparin, N, Zhang, L., Gavin, T. and LoPachin, R M. Enolate-Forming Phloretin Pharmacophores: Hepatoprotection in an Experimental Model of Drug-Induced Toxicity J Pharmacol. Exp. Ther. 357, epub 2016.

Griffith T N, Varela-Nallar L, K Dinamarca M C and Inestrosa N C (2010) Neurobiological effects of hyperforin and its potential in Alzheimer's disease therapy. *Curr Med Chem* 17: 391-406.

Hatcher H, Planalp R, Cho J, Torti F M and Torti S V (2008) Curcumin: from ancient medicine to current clinical trials. *Cell Mol. Life Sci.* 65: 1631-1652.

Head E. (2009) Oxidative damage and cognitive dysfunction: antioxidant treatments to promote healthy brain aging. Neurochem. Res. 34: 670-6781 qbal K and Grundke-Iqbal I (2010) Alzheimer's disease: a multifunctional disorder seeking multitherapies. *Alzheimer & Dementia* 6: 420-424.

Jaeschke H, Williams C D and McGill M R (2012) Caveats of using acetaminophen hepatotoxicity models for natural product testing. *Tox Letters* 215: 40-41.

Kamat C D, Gadal S, Mhatre M. Williamson K S, Pye Q N and Hensley K. (2008) Antioxidants in central nervous system diseases: preclinical promise and translational challenges. *J Alzheimers Dis.* 15: 473-493.

Kim M M and Kim S K (2010) Effect of phloroglucinol on oxidative stress and inflammation. *Food Chem Toxicol* 48: 2925-2933.

Kim H S, Lee K, Kang K A, Lee N H, Hyun J W (2012) Phloroglucinol exerts protective effects against oxidative stress—induced cell damage in SH-SYSY cells. *J. Pharmacol Sci* 119: 186-192.

Lambert S D, Sang S and Yang C S (2007) Possible controversy over dietary polyphenols: benefits vs risks. *Chem Res Toxicol* 20: 583-585.

LoPachin R M, Gavin T, Geohagen B C, Zhang L, Casper D, Lekhrag R and Barber D S (2011) β-Dicarbonyl enolates: a new class of neuroprotectants *J Neurochem* 116: 132-143.

LoPachin R M, Gavin T, DeCaprio A P, Barber D S (2012) Application of the hard and soft acids and bases (HSAB) theory to toxicant-target interactions. *Chem Res Toxicol* 25: 239-251.

LoPachin R M and Gavin T. (2014). Molecular mechanisms of aldehyde toxicity: a chemical perspective. *Chem. Res. Toxicol.* 27, 1081-1091.

Mathiesen L, Malterud K E and Sund R B (1997) Hydrogen bond formation as basis for radical scavenging activity: a structure-activity study of C-methylated dihydrochalcones from Myrica gale and structurally related acetophenones. *Free Rad Biol Med* 22: 307-311.

Mammino L (2013) Investigation of the antioxidant properties of hyperjovinol A through its Cu(II) coordination ability. *J. Mol Model* 19: 2127-2142.

Piao M J, Ahn M J, Kang K A, Kim K C, Zheng J, Yao C W, et al. (2014) Phloroglucinol inhibits ultraviolet B radiation-induced oxidative stress in the mouse skin. *Int J Rad Biol.* 16: 1-8.

Rezk B M, Haenen G R M M, van der Vijgh W. J. F. and Bast A. (2002) The antioxidant activity of phloretin: the disclosure of a new antioxidant pharmacophore in flavonoids. *Biochem Biophys Res Comm.* 295: 9-13.

Ryu J, Zhang R, Hong B H, Yang E J, Kang K A, Choi M, Kim K C, Noh S J, Kim H S, Lee N H, Hyun J W, Kim H S (2013). Phloroglucinol attenuates motor functional deficits in an animal model of Parkinson's disease by enhancing Nrf2 activity. *PLoS One* 8: e71178.

Sappington et al. (2005) The ethyl pyruvate analogues, diethy oxaloproprionate, 2-acetamidoacrylate, and methyl-2-acetamidoacrylate, exhibit anti-inflammatory properties in vivo and/or in vitro. Biochem Pharmacol 70, 1579-1592.

Singh IP and Bharate S B (2006) Phlororglucinol compounds of natural origin. *Nat. Prod. Rep.* 23: 558-591.

Singh I P, Sidana J, Bansal P and Foley W J (2009) Phloroglucinol compounds of therapeutic interest: global patent and technology status. *Exp Opin. Ther Patents* 19: 847-866.

Singh M, Arseneault M, Sanderson T., Murthy V and Ramassamy C. (2008) Challenges for research on polyphenols from foods in Alzheimer's disease: bioavailability, metabolism and cellular and molecular mechanisms. *J Agric Food Chem* 56: 4855-4873.

So M J and Cho E J (2014) Phloroglucinol attenuates free radical-induced oxidative stress. *Prev Nutr Food Sci* 19: 129-135.

Wurglics M and Schubert-Zsilavecz M (2006) Hepericum perforatum: a modern herbal antidepressant: pharmacokinetics of active ingredients. *Clin Pharmacokinet* 45: 449-468.

Youdim K A and Joseph J. A. (2001) A possible emerging role of phytochemicals in improving age-related neurological dysfunctions: a multiplicity of effects. *Free Rad Biol Med.* 30: 583-594.

Zanoli P (2004) Role of hyperforin in the pharmacological activities of St. John's Wort. *CNS Drug Rev.* 10: 203-218.

Zhu Q, Zhang N Q, Lau C F, Chao J, Sun Z, Chang C C, Chen F and Wang M. (2012) In vitro attenuation of acrolein-induced toxicity by phloretin, a phenolic compound from apple. *Food Chem.* 135: 1762-1768.

What is claimed is:

1. A method of treating a toxicity due to a therapeutic agent or an agent that causes oxidative cellular damage in a subject receiving the agent, the method comprising administering to the subject a compound of formula (I)

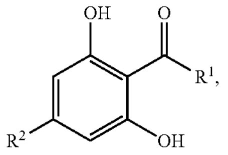

(I)

or a tautomer thereof; or a geometric or optical isomer thereof; or racemate thereof; or a pharmaceutically acceptable salt thereof, in an amount effective to reduce the toxicity due to the agent, wherein:

$R^1$ and $R^3$ are independently alkyl, alkenyl, aryl, aralkyl, cycloalkyl, heteroaryl, heteroaralkyl or heterocycloalkyl;

$R^2$ is $NH_2$, $NHCOR^3$, NH-alkyl, N,N-dialkyl, cyclic N,N-di alkyl, SH, S-alkyl, S-aryl, aryl, heteroaryl, or $NR^4R^5$; and $R^4$ and $R^5$ are independently alkyl or NH-alkyl, or $R^4$ and $R^5$ can form a ring with each other, and any ring so formed is heteroaromatic, and any ring so formed may contain one or more N, O and/or S atoms;

wherein any aryl, aralkyl, cycloalkyl, heteroaryl, heteroaralkyl, or heterocycloalkyl ring can be independently substituted with =O, OH, halogen, $CH_3$ or $NH_2$; and wherein any alkyl can independently be branched or unbranched.

2. The method of claim 1, wherein the therapeutic agent is acetaminophen, diclofenac, cyclophosphamide, valproic acid, clopidogrel, esomeprazole, atorvastatin, duloxetine, raloxifene, a platinum containing antineoplatstic agent, or radiation used in radiation therapy.

3. The method of claim 2, wherein the platinum containing antineoplatstic agent is cisplatin.

4. The method of claim 1, wherein the agent that causes oxidative cellular damage is tobacco smoke, acrolein, alcohol, or a radiocontrast agent.

5. The method of claim 1, wherein the agent is a polarizable electrophile.

6. The method of claim 1, wherein the toxicity is hepatotoxicity, neurotoxicity, or toxicity due to oxidative cellular stress.

7. The method of claim 1, wherein the compound of formula (I) and the agent are administered to the subject at the same time.

8. The method of claim 7, wherein the compound of formula (I) and the agent are administered in the same formulation.

9. The method of claim 1, wherein the compound of formula (I) is administered to the subject before administration of the agent to the subject.

10. The method of claim 1, wherein the compound of formula (I) is administered to the subject after administration of the agent to the subject.

11. The method of claim 1, wherein the compound of formula (I) is administered by parenteral administration.

12. The method of claim 1, wherein the compound of formula (I) is formulated with an enteric coating and the compound is administered orally.

13. The method of claim 1, wherein the compound of formula (I) prevents or reduces hepatotoxicity.

14. The method of claim 1, wherein:

$R^1$ is alkyl, cycloalkyl, or

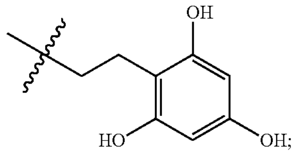

and $R^2$ is $NH_2$, $NHCOR^3$, NH-alkyl, SH, S-alkyl, S-aryl or

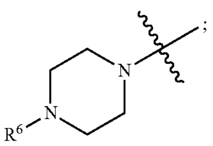

wherein $R^6$ is hydrogen or alkyl.

15. The method of claim 1, wherein the compound of formula (I) is:

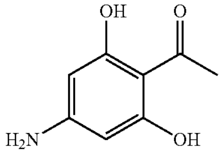

,

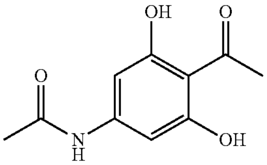

,

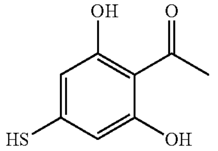

,

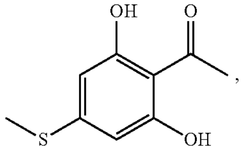

,

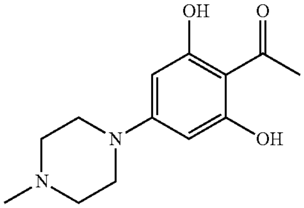

or

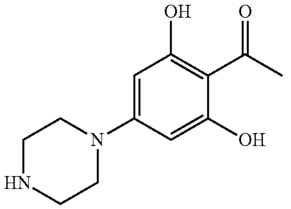

.

or a tautomer thereof; or a geometric or optical isomer thereof; or racemate thereof; or a pharmaceutically acceptable salt thereof.

* * * * *